United States Patent
Berryman et al.

(12)

(10) Patent No.: US 6,291,678 B1
(45) Date of Patent: Sep. 18, 2001

(54) PROCESS FOR THE PREPARATION OF CHIRAL KETO-HETEROCYCLES OF BASIC AMINO ACIDS

(75) Inventors: Kent A. Berryman; Annette M. Doherty, both of Ann Arbor; Jeremy J. Edmunds, Ypsilanti; Janet S. Plummer, Dexter, all of MI (US)

(73) Assignee: Warner-Lambert Company, Ann Arbor, MI (US)

( * ) Notice: Subject to any disclaimer, the term of this patent is extended or adjusted under 35 U.S.C. 154(b) by 0 days.

(21) Appl. No.: 09/202,377

(22) PCT Filed: May 30, 1997

(86) PCT No.: PCT/US97/09496

§ 371 Date: Dec. 11, 1998

§ 102(e) Date: Dec. 11, 1998

(87) PCT Pub. No.: WO97/48687

PCT Pub. Date: Dec. 24, 1997

Related U.S. Application Data

(60) Provisional application No. 60/019,988, filed on Jun. 18, 1996.

(51) Int. Cl.$^7$ .................................................. C07D 277/28

(52) U.S. Cl. ............................................. 546/209; 548/200
(58) Field of Search ........................... 548/200; 546/209; 514/326–365

(56) References Cited

U.S. PATENT DOCUMENTS 5,827,866 * 10/1998 Costanzo ............................... 514/369
6,020,331 * 2/2000 Kahn ..................................... 514/221

FOREIGN PATENT DOCUMENTS

96/30035 10/1996 (WO) .

OTHER PUBLICATIONS

Greene Protective Groups in Organic Syntheis pp.379–382, 1991.*

Edwards, P. D., et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole,"*Journal of the American Chemical Society*, 1992, vol. 114, No. 5, pp. 1854–1863.

Deng, J., et al., "Synthesis of Cyclotheonamide B and Its Derivatives," *Angew. Chem. Int. Ed. Engl.*, 1994, vol. 33, No. 17, pp. 1729–1731.

Edwards, P. D., et al., "Peptidyl α–Ketoheterocyclic Inhibitors of Human Neutrophil Elastase. 2. Effect of Varying the Heterocyclic Ring on in Vitro Potency," *Journal of Medicinal Chemistry*, 1995, vol. 38, No. 1, pp. 76–85.

Guichard, G., et al., "Synthesis of Arginine Aldehydes for the Preparation of Pseudopeptides," *Peptide Research*, 1993, vol. 6, No. 3, pp. 121–124.

Hagihara, M. and Schreiber, S. L., "Reassignment of Stereochemistry and Total Synthesis of the Thrombin Inhibitor Cyclotheonamide B," *Journal of the American Chemical Society*, 1992, vol. 114, No. 16, pp. 6570–6571.

International Search Report (PCT/US 97/09496).

Costanzo, M. J., et al., "Potent Thrombin Inhibitors That Probe S$_1$ Subsite: Tripeptide Transition State Analogues Based on a Heterocycle–Activated Carbonyl Group," *Journal of Medicinal Chemistry*, 1996, vol. 39, No. 16, pp. 3039–3043.

* cited by examiner

Primary Examiner—Robert Gerstl
(74) *Attorney, Agent, or Firm*—Merchant & Gould P.C.

(57) ABSTRACT

A process for the preparation of novel keto heterocycle derivatives of basic natural and unnatural amino acids which affords products of high enantiomeric excess where a metalated heterocycle is reacted with N,O-dialkyl amide of an amino acid containing arylsulphonamide protected side chain amine in high chemical and optical yield as well as the novel compounds obtained by the process.

5 Claims, No Drawings

PROCESS FOR THE PREPARATION OF CHIRAL KETO-HETEROCYCLES OF BASIC AMINO ACIDS

This application claims benefit to Provisional Application 60/019,988 filed Jun. 18, 1996.

BACKGROUND OF THE INVENTION

The present invention relates to the preparation of keto heterocycle derivatives of amino acids that have utility in the preparation of biologically active substances. These derivatives may, for example, be incorporated in inhibitors of serine proteases such as thrombin, Factor Xa, and Factor VIIa. As such these inhibitors have utility in the treatment of diseases that result from abnormal coagulation. Typical pathologic conditions include, for example, venous and arterial thrombosis, atrial fibrillation, stroke, restenosis, and recurrent myocardial infarction. These compounds are useful for preventing or treating unstable angina, refractory angina, disseminated intravascular coagulation, and ocular build up of fibrin. Since thrombin has also been demonstrated to activate a number of different cell types, these compounds are useful for the treatment or prophylaxis of septic shock and other inflammatory responses such as acute or chronic atherosclerosis. The compounds also have utility in treating neoplasia/metastasis and neurodegenerative diseases such as Alzheimer's and Parkinson's disease.

Previously peptidyl keto heterocycles have been prepared by conversion of cyano hydrins to imino ethers derivatives and cyclisation with, for example, amino phenols to afford peptidyl-keto-benzoxazoles (Edwards P D, et al., *J. Am. Chem. Soc.*, 114, 1854 (1992)). Alternatively addition of lithiated heterocycles to N,O-dimethyl amides of the amino acid valine has been shown to proceed in good chemical and optical yield (Edwards P D, et al., *J. Med. Chem.*, 38, 76 (1995)). While the N,O-dimethyl amide of BOCNH-Arg (Mtr) has been used to prepare keto amides (Deng J, et al., *Angew. Chem. Int. Ed. Engl.*, 33 (17),1729 (1994)), and in failed attempts to prepare arginals (Guichard G, et al., *Pept. Res.*, 6, 121 (1993)) they have not previously found use in the preparation of keto heterocycle basic amino acid derivatives.

SUMMARY OF THE INVENTION

Accordingly, a first aspect of the present invention is a novel process for the preparation of a compound of Formula I (D(-)) or Formula I (L(+))

I(D(-))

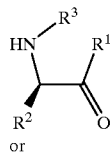

or

I(L(+))

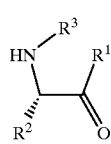

wherein $R^1$ is

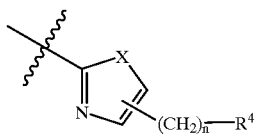

wherein X is O,
S, or
$NR^5$ wherein $R^5$ is H,
alkyl,
alkenyl,
alkynyl,
cycloalkyl,
cycloalkylalkyl,
aryl, or
arylalkyl,
n is zero or an integer of 1 to 4, and
$R^4$ is H,
halogen,
$NHR^5$ wherein $R^5$ is as defined above,
$NR^5(R^{5a})$ wherein $R^5$ and $R^{5a}$ are the same or different and are as defined above for $R^5$
$OR^5$ wherein $R^5$ is as defined above,
$NO_2$,
CN,
$SO_4R^5$ wherein $R^5$ is as defined above,
$C(=O)NR^5R^{5a}$) wherein $R^5$ and $R^{5a}$ are the same or different and are as defined above for $R^5$,
$CO_2R^5$ wherein $R^5$ is as defined above,
$C(=O)R^5$ wherein $R^5$ is as defined above,
aryl, or
heteroaryl,

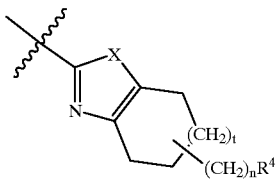

wherein t is zero or an integer of 1 to 3, and X, n, and $R^4$ are as defined above,

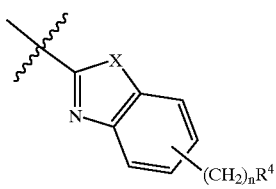

wherein X, n, and $R^4$ are as defined above,

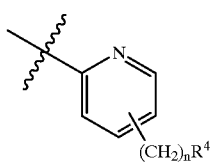

wherein n and $R^4$ are as defined above,

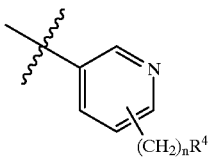

wherein n and $R^4$ are as defined above,

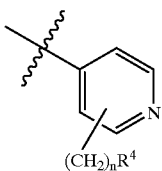

wherein n and $R^4$ are as defined above,

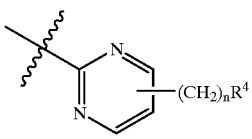

wherein n and $R^4$ are as defined above,

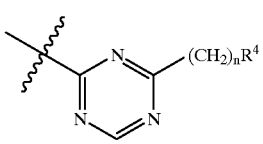

wherein n and $R^4$ are as defined above;

$R^2$ is —$(CH_2)_q$—Y wherein Y is

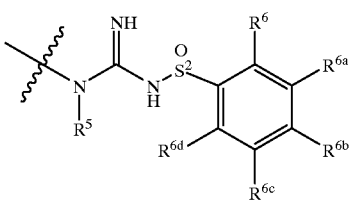

wherein $R^5$ is as defined above, and $R^6, R^{6a}, R^{6b}, R^{6c}, R^{6d}$ are the same or different and are H, alkyl,
alkenyl,
alkynyl,
cycloalkyl, or $OR^5$ wherein $R^5$ is as defined above,

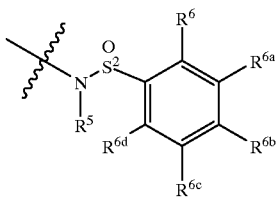

wherein $R^5, R^6, R^{6a}, R^{6b}, R^{6c},$ and $R^{6d}$ are as defined above,

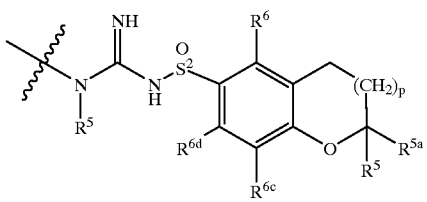

wherein p is zero or an integer of 1 to 2, and $R^5 R^{5a}, R^6, R^{6c},$ and $R^{6d}$ are as defined above, or

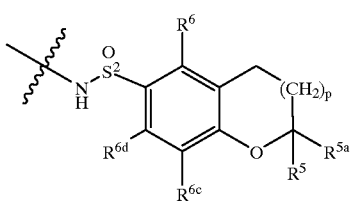

wherein p, $R^5, R^{5a}, R^6 R^{6c},$ and $R^{6d}$ are as defined above, and q is an integer of 3 to 6,

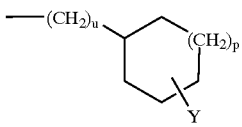

wherein u is zero or an integer of one, and p and Y are as defined above,

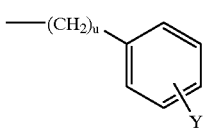

wherein u and Y are as defined above,

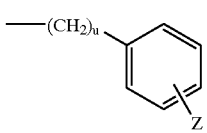

wherein Z is

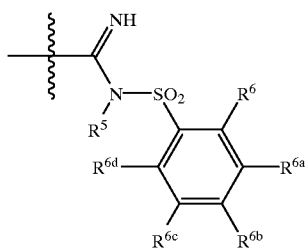

wherein $R^5$, $R^6$, $R^{6a}$, $R^{6b}$, $R^{6c}$, and $R^{6d}$ are as defined above, or

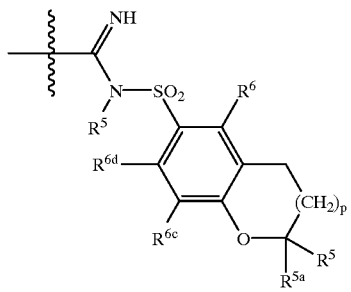

wherein p, $R^5$, $R^{5a}$, $R^6$, $R^{6c}$, and $R^{6d}$ are as defined above, and

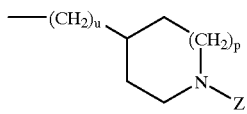

wherein u is as defined above,

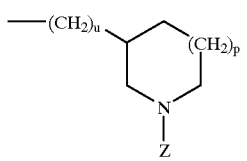

wherein u, p, and Z are as defined above,

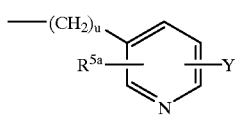

wherein u, $R^{5a}$, and Y are as defined above,

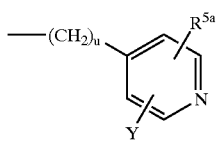

wherein u, $R^{5a}$, and Y are as defined above,

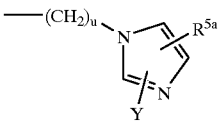

wherein u, $R^{5a}$, and Y are as defined above,

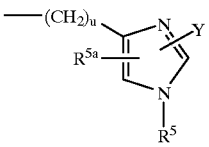

wherein u, R $R^{5a}$, and Y are as defined above,

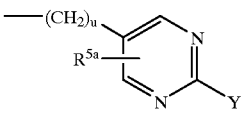

wherein u, $R^{5a}$, and Y are as defined above, or

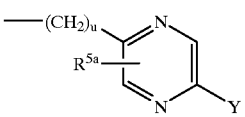

wherein u, $R^{5a}$ and Y are as defined above; and $R^3$ is H,

—$CO_2R^7$ wherein $R^7$ is alkyl,
cycloalkyl,
cycloalkylalkyl,
arylalkyl, or
aryl, or

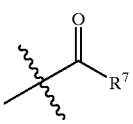

wherein $R^7$ is as defined above; or an addition salt thereof; which comprises:

step (a) treating a compound of Formula IIIa (D(−)) or Formula IIIa (L(+))

IIIa (D(-))

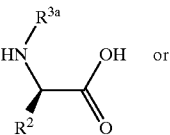

-continued

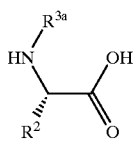
IIIa (L(+))

wherein $R^{3a}$ is $CO_2R^7$, wherein $R^7$ is as defined above, or

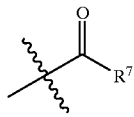

wherein $R^7$ is as defined above, and $R^2$ is as defined above;

with an activating reagent in a solvent to afford an activated acyl intermediate which is treated with a compound of formula:

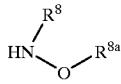

wherein $R^8$ and $R^{8a}$ may be the same or different and are
alkyl,
cycloalkyl,
cycloalkylalkyl, or
$R^8$ and $R^{8a}$ may be joined to form a ring of from 4 to 8 atoms, to afford a compound of Formula IIa (D(−)) or Formula IIa (L(+))

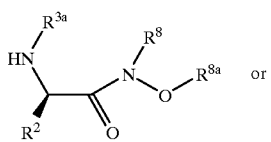
IIa (D(−))

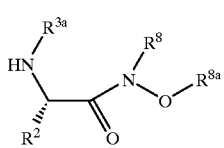
IIa (L(+))

wherein $R^2$, $R^{3a}$, $R^8$, and $R^{8a}$ are as defined above;

step (b) treating a compound of Formula IIa (D(−)) or Formula IIa (L(+)) with a compound of Formula IV $$R^1\text{—M} \qquad\qquad\qquad IV$$

wherein M is lithium, cerium halide, titanium alkoxide, titanium halide, or magnesium halide and $R^1$ is as defined above, in a solvent to afford a compound of Formula Ia (D(−)) or Formula Ia (L(+))

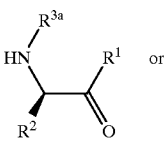
Ia (D(−))

Ia (L(+))

wherein $R^1$, $R^2$, and $R^{3a}$ are as defined above;

step (c) treating a compound of Formula Ia (D(−)) or Formula Ia (L(+)) with a deprotecting reagent in a solvent to afford a compound of Formula Ib (D(−)) or Formula Ib (L(+))

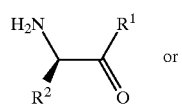
Ib (D(−))

Ib (L(+))

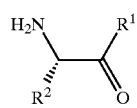

wherein $R^1$ and $R^2$ are as defined above.

A second aspect of the present invention is a novel compound of Formula I (D(−)) or Formula I (L(+))

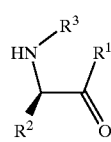
I(D(−))

or

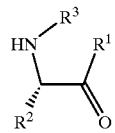
I(L(+))

wherein $R^1$, $R^2$, and $R^3$ are as defined above; or an addition salt thereof.

DETAILED DESCRIPTION OF THE INVENTION

In the compounds of the present invention, the term "alkyl" means a straight or branched hydrocarbon radical having from 1 to 6 carbon atoms and includes, for example, methyl, n-propyl, tert-butyl, and the like.

The term "alkenyl" means a straight or branched unsaturated hydrocarbon radical having from 2 to 6 carbon atoms and includes, for example, 2-butenyl, 3-methyl-3-butenyl, 1-hexenyl, and the like.

The term "alkynyl" means a straight or branched triple bonded unsaturated hydrocarbon radical having from 2 to 6 carbon atoms and includes, for example, 2-butynyl, 3-hexynyl, and the like.

The term "cycloalkyl" means a saturated hydrocarbon radical having from 3 to 12 carbon atoms and includes, for example, cyclopropyl, cyclopentyl, and the like.

The term "cycloalkylalkyl" means a cycloalkyl group attached to an alkyl group wherein "cycloalkyl" and "alkyl" are as defined above and includes, for example, cyclopropylmethyl, cyclopentylethyl, and the like.

The term "alkyloxy" is O-alkyl as defined above for alkyl.

The term "aryl" means an aromatic radical which is a phenyl or naphthyl group, which may be unsubstituted or substituted by 1 to 5 substituents selected from, alkyl, alkyloxy, wherein the alkyl or alkyloxy substituents may be part of a ring occupying two adjacent ring positions and includes, for example, dihydrobenzopyrans, benzo-1,3-dioxole, and the like.

The term "arylalkyl" means an aromatic radical attached to an alkyl radical wherein "aryl" and "alkyl" are as defined above and includes for example benzyl, and naphthylmethyl.

The term "heteroaryl" means a heteroaromatic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-triazolyl, tetrazolyl, 2-, 3-, or 4-pyridinyl, 3-, 4-, or 5-pyridazinyl, 2-pyrazinyl, 2-, 4-, or 2-, 4-, or 5-pyrimidinyl, 2-, 3-, 4-, 5-, 6-, 7-, or 8-quinolinyl, 2-, 3-, 4-, 5-, 6-, or 7-indolyl, 2-, 3-, 4-, 5-, 6-, or 7-benzothienyl, 2-, 4-, 5-, 6-, or 7-benzoxazolyl, 2-, 4-, 5-, 6-, or 7-benzimidazolyl unsubstituted or substituted by 1 to 4 substituents selected from alkyl as defined above or alkyloxy as defined above, hydroxy, thiol, nitro, halogen, formyl, amino, $CONH_2$, $CO_2$alkyl, ketone, or nitrile.

The term "halogen" means fluorine, chlorine, bromine, or iodine.

Compounds of the present invention are capable of forming acid addition salts (see for example, Berge SM, et al., *Pharmaceutical Salts, Journal of Pharmaceutical Science*, 66, 1–10 (1977)) with inorganic acids such as for example hydrochloric acid, sulfuric acid, and the like as well as salts derived from organic acids such as for example aliphatic mono and dicarboxylic acids or aliphatic and aromatic sulphonic acids. The acid addition salts are prepared by contacting the free base form with a sufficient amount of the desired acid to produce the salt. The free base form may be regenerated by contacting the salt form with a base. While the free base more may differ from the salt form in terms of physical properties, such as solubility, the salts are equivalent to their respective free bases for the purposes of the present invention. Certain compounds of the present invention can exist in unsolvated form as well as solvated form including hydrated form. In general the solvated form, including hydrated form are equivalent to unsolvated form and are intended to be encompassed within the scope of the present invention. In some situations compounds of the present invention form diastereomers as a result of an additional chiral center. Therefore all stereoisomers are considered to be included in this invention.

The following table provides a list of abbreviations and definitions thereof used in the present invention.

| Abbreviation | Description |
|---|---|
| BOC | tertiary-butyloxycarbonyl |
| MTR | 2,3,6-trimethyl-4-methoxybenzenesulphonyl |
| PMC | 2,2,5,7,8-pentamethylchroman-6-sulfonyl |
| TFA | trifluoroacetic acid |
| BOP-reagent | benzotriazol-1-yloxy-tris (dimethylamino) phosphonium hexafluorophosphate |
| THF | tetrahydrofuran |
| EtOAc | ethylacetate |
| TMEDA | N,N,N',N'-tetramethylethylenediamine |
| HMPA | hexamethylphosphoramide |
| DCC | dicyclohexyl carbodiimide |
| DMF | dimethyl formamide |
| HF | hydrogen fluoride |
| DIEA | diisopropylethylamine |
| r.t. | room temperature |
| Phe | phenylalanyl |
| Pip | pipecolyl |
| Arg | arginyl or arginine |
| MOT | mean occlusion time |
| aPTT | activated partial thromboplastin time |
| TT | thrombin time |
| MS (ES) | mass spectrometry (electro spray) |
| MS (CI) | mass spectrometry (chemical ionization) |
| MS (APCI) | mass spectrometry (atmospheric pressure CI) |
| NMM | N-methylmorpholine |
| IBCF | iso-butyl chloroformate |
| nBuLi | n-butyl lithium |
| HCl | hydrogen chloride |
| $NH_4Cl$ | ammonium chloride |
| PMC-Cl | 2,2,5,7,8-pentamethylchroman-6-sulfonyl chloride |
| $NaHSO_4$ | sodium hydrogen sulfate |
| AcOH | acetic acid |
| PD/C | palladium on carbon |
| NaOH | sodium hydroxide |
| $PtO_2$ | platinum oxide |
| 1H NMR | proton magnetic resonance |
| DMSO | dimethylsulfoxide |
| $CDCl_3$ | deuterochloroform |

The process of the present invention in its first aspect is outlined in Scheme I.

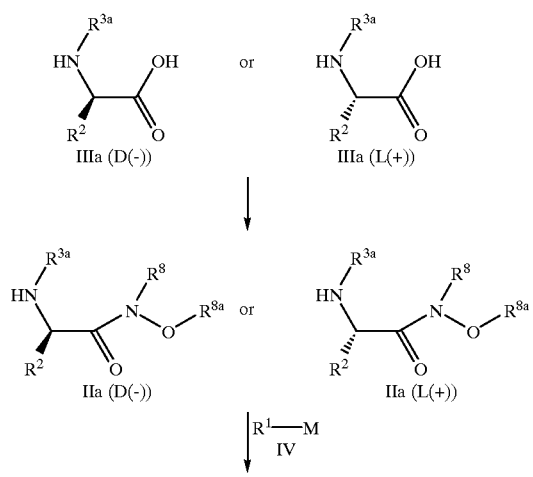

SCHEME I

-continued

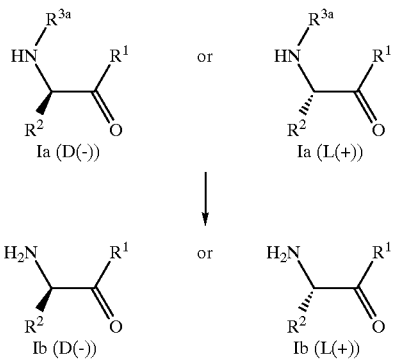

Ia (D(-))      Ia (L(+))

↓

Ib (D(-))      Ib (L(+))

A compound of Formula III (D(-)) or Formula III (L(+))

IIIa (D(-))

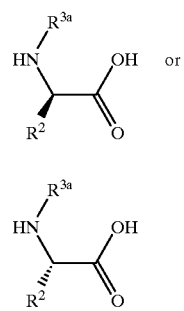

IIIa (L(+))

$R^6$ is —$(CH_2)_q$—Y wherein Y is

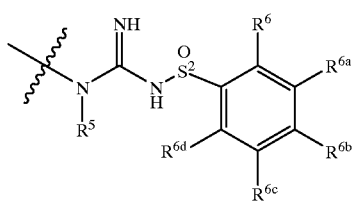

wherein $R^5$ is H,
  alkyl,
  alkenyl,
  alkynyl,
  cycloalkyl,
  cycloalkylalkyl,
  aryl, or
  arylalkyl, and
$R^6$, $R^{6a}$, $R^{6b}$, $R^{6c}$, and $R^{6d}$ are the same or different and are
  H,
  alkyl,
  alkenyl,
  alkynyl,
  cycloalkyl, or $OR^5$ wherein $R^5$ is as defined above,

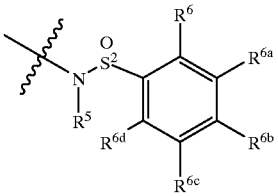

wherein $R^5$ $R^6$, $R^{6a}$, $R^{6b}$, $R^{6c}$, and $R^{6d}$ are as defined above,

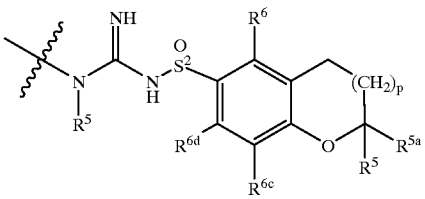

wherein p is zero or an integer of 1 to 2,
  $R^5$ and $R^{5a}$ are the same or different and are as defined above or $R^5$, and $R^6$, $R^{6c}$ and $R^{6d}$ are as defined above, or

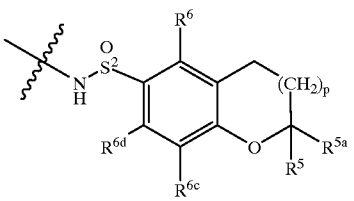

wherein p, $R^5$, $R^{5a}$, $R^6$, $R^{6c}$, and $R^{6d}$ are as defined above, q is an integer of 3 to 6,

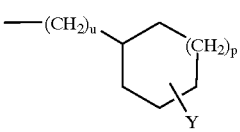

wherein u is zero or an integer of one, and p and Y are as defined above,

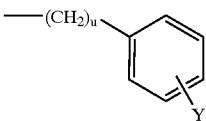

wherein u and Y are as defined above,

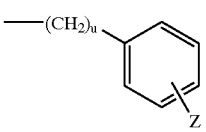

wherein Z is

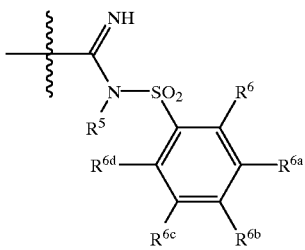

wherein $R^5$, $R^6$, $R^{6a}$, $R^{6b}$, $R^{6c}$, and $R^{6d}$ are as defined above, or

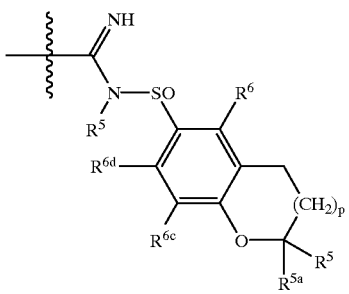

wherein p, $R^5$, $R^{5a}$, $R^6$ $R^{6c}$, and $R^{6d}$ are as defined above, and wherein u is as defined above,

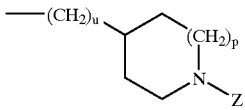

wherein u, p, and Z are as defined above,

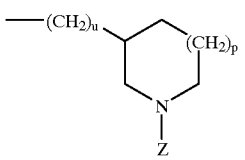

wherein u, p, and Z are as defined above,

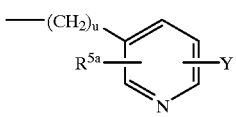

wherein u, $R^{5a}$, and Y are as defined above,

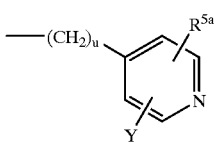

wherein u, $R^{5a}$, and Y are as defined above,

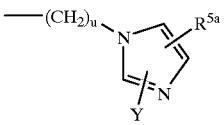

wherein u, $R^{5a}$, and Y are as defined above,

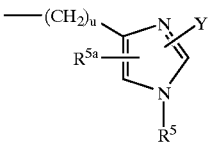

wherein u, $R^{5a}$, and Y are as defined above,

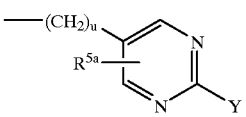

wherein u, $R^{5a}$, $R^5$, and Y are as defined above,

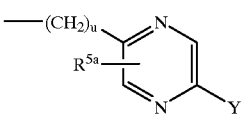

wherein u, $R^{5a}$, and Y are as defined above, or

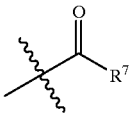

wherein u, $R^{5a}$, and Y are as defined above; and $R^{3a}$ is —$CO_2R^7$
wherein $R^7$ is alkyl,
cycloalkyl,
cycloalkylalkyl,
arylalkyl, or
aryl, or

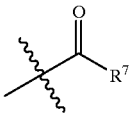

wherein $R^7$ is as defined above;
is treated with an activating reagent such as, for example, oxalyl chloride, thionyl chloride, diisopropyl carbodiimide, dicyclohexyl carbodiimide, 1,1'-carbonyl-diimidazole, 2-chloro-1-methylpyridinium iodide, 2-ethoxy-1-ethoxycarbonyl-1,2-dihydro-quinoline, benzotriazole-1-yl-oxy-tris-pyrrolidino-phosphonium hexafluorophosphate, bromo-tris-pyrrolidino-phosphonium hexafluorophosphate, 2-(1H-benzotriazole-1-yl)-1,1,3,3-tetramethyluronium tetrafluoroborate, 1-ethyl-3-(3'-dimethylaminopropyl) carbodiimide, BOP-reagent, alkyl chloroformate, and the like in a solvent, such as, for example, ethyl acetate, tetrahydrofuran, methylene chloride, and the like at a temperature of about −78° C. to about 25° C., to afford an activated acyl intermediate which is directly treated with a compound of formula

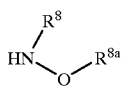

wherein $R^8$ and $R^{8a}$ may be the same or different and are
alkyl,
cycloalkyl,
cycloalkylalkyl, or
$R^8$ and $R^{8a}$ may be joined to form a ring of from 4 to 8 atoms (or salt thereof and base) to afford a compound of Formula IIa (D(-)) or Formula IIa (L(+))

IIa (D(-))

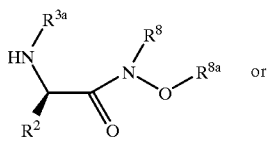

or

IIa (L(+))

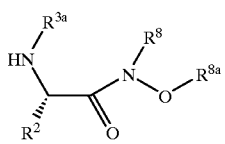

wherein $R^2$, $R^{3a}$, $R^8$, and $R^{8a}$ are as defined above.

Preferably, the reaction is carried out in isobutylchloroformate in the presence N-methyl-morpholine in methylene chloride at about −15° C. to about 25° C. The N,O-dialkylhydroxylamine, i.e.,

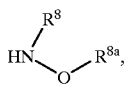

is preferably N,O-dimethylhydroxyl amine.

A compound of Formula IIa (D(−) or Formula IIa (L+) is treated with a compound of Formula IV $R^1$—M  IV wherein M is lithium, cerium halide, titanium alkoxide, titanium halide, or magnesium halide and $R^1$ is

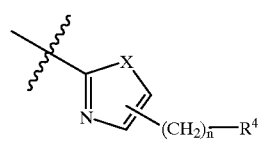

wherein X is O,
S, or
$NR^5$ wherein $R^5$ is as defined above,
n is zero or an integer of 1 to 4, and
$R^4$ is H,
halogen,
$NHR^5$ wherein $R^5$ is as defined above,
$NR^5(R^{5a})$ wherein $R^5$ and $R^{5a}$ are the same or different and are as defined above for $R^5$,
$OR^5$ wherein $R^5$ is as defined above,
$NO_2$,
CN,
$SO_4R^5$ wherein $R^5$ is as defined above,
$C(=O)NR^5(R^{5a})$ wherein $R^5$ and $R^{5a}$ are the same or different and are as defined above for $R^5$,
$CO_2R^5$ wherein $R^5$ is as defined above,
$C(=O)R^5$ wherein $R^5$ is as defined above,
aryl, or
heteroaryl,

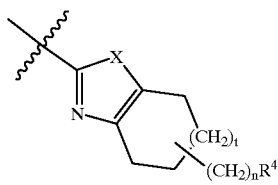

wherein t is zero or an integer of 1 to 3, and X, n, and $R^4$ are as defined above,

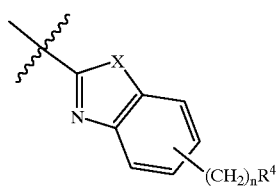

wherein X, n, and $R^4$ are as defined above,

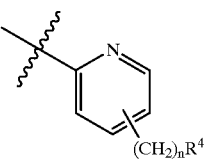

wherein n and $R^4$ are as defined above,

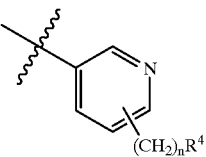

wherein n and $R^4$ are as defined above,

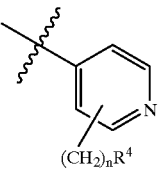

wherein n and $R^4$ are as defined above,

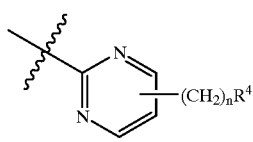

wherein n and $R^4$ are as defined above,

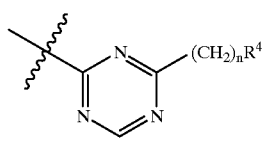

wherein n and $R^4$ are as defined above,
in a solvent such as, for example, diethyl ether, tetrahydrofuran, and the like or a nonethereal solvent which does not react with a compound of Formula IV, such as methylene chloride and the like, at about −78° C. to about 25° C. to afford a compound of Formula Ia (D(−)) or Formula Ia (L(−))

Ia (D(−))

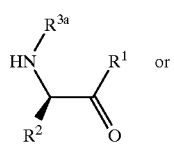

Ia (L(+))

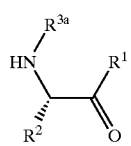

wherein $R^1_1$ $R^2$, and $R^{3a}$ are as defined above. Preferably, M is lithium, the solvent is THF, and the use of TMEDA or HMPA is optional.

A compound of Formula Ia (D(−)) or Formula Ia (L(+)) is treated with a conventional deprotecting reagent (for example see "Protective groups in organic synthesis" Greene TW and Wuts PGM, Wiley (1991)) known to those skilled in the art of organic synthesis, in a solvent such as, for example, dioxane and the like at about 25° C. to afford compounds of Formula 1b (D(−)) or Formula Ib (L(+)).

Ib (D(−))

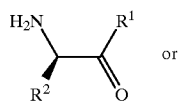

Ib (L(+))

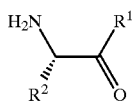

wherein $R^1$ and $R^2$ are as defined above.

Preferably, a compound of Formula Ia(D(−)) or Formula Ib(L(+)) wherein $R^{3a}$ is tert-butoxycarbonyl (BOC) for example, are deprotected with an acid such as, for example, hydrogen chloride in dioxane at about 25° C. to afford compounds of Formula Ib (D(−)) or Formula Ib (L(+)).

Compounds of Formula Ib (D(−)) or Formula Ib (L(+))

Ib (D(−))

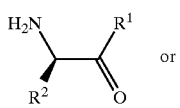

Ib (L(+))

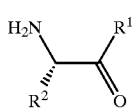

wherein $R^1$ and $R^2$ are as defined above may then be reacted with activated acids to afford amides as shown in Scheme II. A typical procedure requires activation of the acid with BOP-reagent and stirring this adduct with a compound of Formula Ib (D(−)) or Formula Ib (L(+)) in DMF for 2 hours. The side chain amine protecting group, which is typically Pmc or Mtr is removed by treatment with TFA at about room temperature for several hours, or alternatively by treatment with a mineral acid such as, for example, anhydrous HF, in the presence or absence of a scavenger such as, for example, anisole, thiophenol, ethylmethyl sulphide, and the like.

SCHEME II

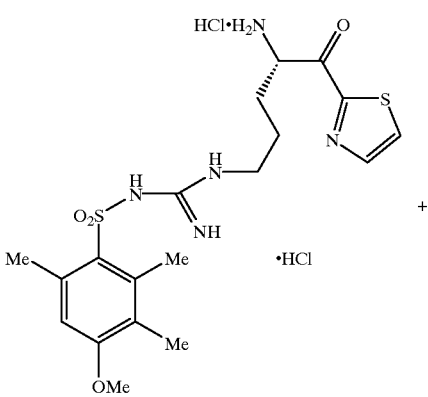

19
-continued

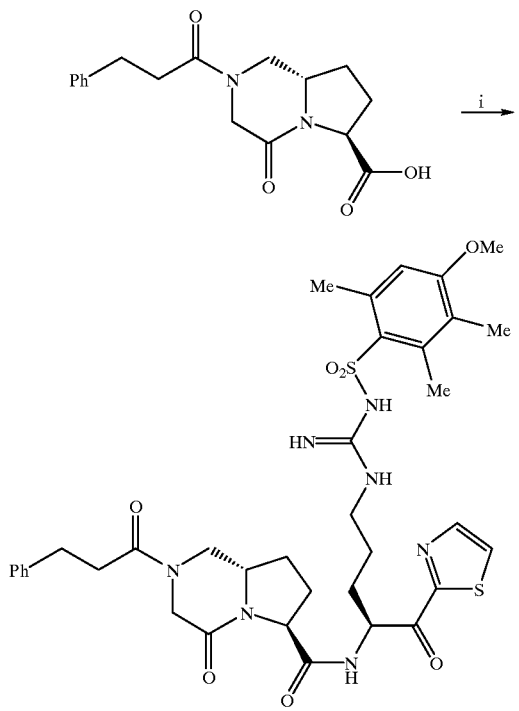

20
-continued

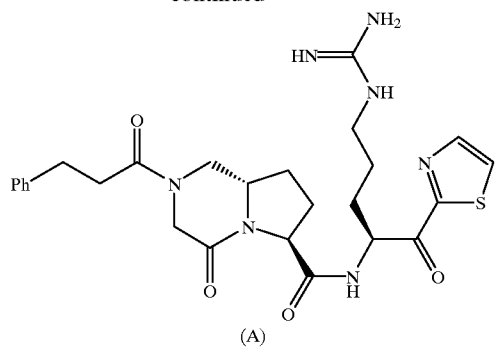

(A)

Reagents: i. BOP-reagent, DMF, DIEA, RT, 3 h (71%); ii. TFA, thioanisole, RT, 2.5 h (45%).

These compounds are inhibitors of the proteolytic activity of serine proteases, typically thrombin as demonstrated by in vitro and in vivo experiments.

In Vitro

The ability of compounds to act as inhibitors of thrombin catalytic activity is assessed by determination of that concentration of test substance that inhibits by 50% ($IC_{50}$) the ability of thrombin to cleave the chromogenic substrate S-2238 (H-D-Phe-L-Pip-L-Arg-p-nitroanilide.2 HCl). Typically thrombin in 10 mM HEPES, 100 mM NaCl, 0.05% BSA, and 0.1% PEG-8000 and the test substance in DMSO are incubated for 60 minutes at room temperature. To this mixture is added S-2238 and the velocity of S-2238 hydrolysis measured by observing the intensity of absorbance at 405 nM over 5 minutes.

A similar protocol is followed to access the trypsin inhibitory activity of the test substances, except thrombin is replaced by trypsin and the chromogenic substrate is S2222 (N-Bz-L-Ile-L-Glu-L-Gly-L-Arg-p-nitroanilide.HCl).

| Example | Structure | Thrombin $IC_{50}$ (nM) | Trypsin $IC_{50}$ (nM) |
|---|---|---|---|
| A | 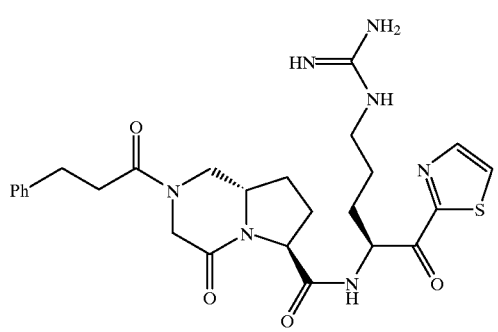 | 5 | 1 |

|         |           | Thrombin       | Trypsin        |
| Example | Structure | IC$_{50}$ (nM) | IC$_{50}$ (nM) |
| ------- | --------- | -------------- | -------------- |
| B       | 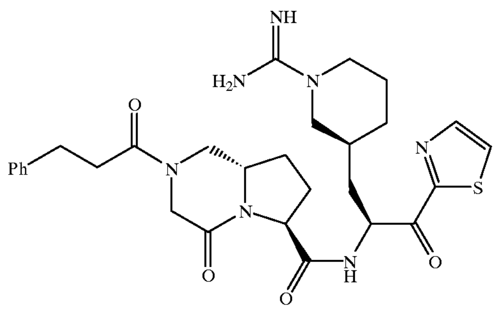          | 30             | 4350           |

In Vivo

The ability of compounds to affect markers of anticoagulant activity in vivo were assessed in a rat arterial model of thrombosis. This model requires injury of the rat carotid artery by the application of a FeCl$_3$ solution. Typically test substances are administered by applying a loading dose of 0.75 mg/kg plus continual infusion of 50 μg/kg/min.

In this model control MOT is 20 minutes, control aPTT is 15 s and control TT is 30 s. The fold shift in aPTT and TT are measured at a 30 minute time point.

| Example | Fold Shift in MOT | Fold Shift in aPTT | Fold Shift in TT |
| ------- | ----------------- | ------------------ | ---------------- |
| A       | 2.4               | 3.2                | 13               |
| B       | >3                | 3.1                | 15               |

The following nonlimiting examples illustrate the inventors' method for preparing the compounds of the present invention.

EXAMPLE 1

(S)-N-[[[4-amino-5-oxo-5-(2-thiazolyl)pentyl]amino]iminomethyl]-4-methoxy-2,3,6-trimethyl-benzenesulfonamide Step (a) Preparation of: 1,1-dimethylethyl (S)-[4-[[imino[[(4-methoxy-2,3,6-trimethylphenyl)sulfonyl]amino]methyl]amino]-1-(methoxymethylamino)carbonyl]butyl] carbamate

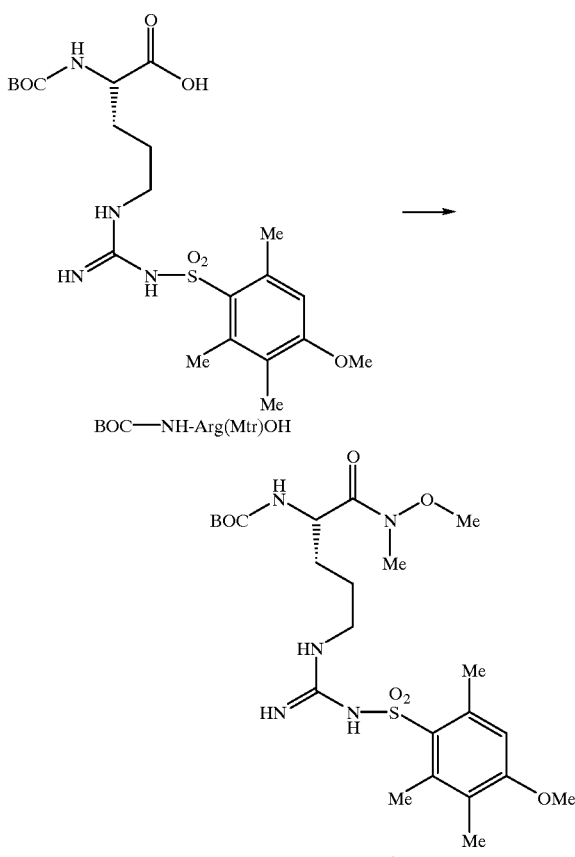

To Boc-NH-Arg(Mtr)OH (6.61 g, 13.6 mmol) in dichloromethane (33 mL) at 0° C. was added N-methyl morpholine (1.65 mL, 15.0 mmol) then isobutyl chloroformate (1.95 mL, 15.0 mmol). Stirred at 0° C. for 30 minutes. Added N,O dimethylhydroxyl amine HCl (1.5 g, 15.4 mmol) and N-methyl morpholine (1.65 mL, 15.0 mmol). Stirred at 0° C. for 45 minutes. Diluted with ethyl acetate (150 mL), washed with 1N HCl (2×80 mL), brine (80 mL), washed with sodium sulfate, filtered, removed solvent in vacuo, and purified with silica gel column eluted with 80% ethyl acetate in hexane to 100% ethyl acetate. Isolated 4.85 g (67.5%) of product (1) as a white foam.

$^1$H NMR (CDCl$_3$, 300 MHz): 6.52 (1H, s), 6.19 (2H, bs), 5.50 (1H, d, J=9.0 Hz) 4.63 (1H, bs), 3.82 (3H, s), 3.72 (3H, s), 3.30 (1H, bs), 3.18 (3H, s), 3.15 (3H, s), 2.69 (3H, s), 2.61 (3H, s), 2.12 (3H, s), 1.50–1.75 (4H, m), 1.41 (9H, s).
(CI MS) M+1=530, M+C$_2$H$_5$=558.

Step (b) Preparation of: 1,1-dimethylethyl (S)-[4-[[imino[[(4-methoxy-2,3,6-trimethylphenyl)-sulfonyl]amino]methyl]amino]-1-[(2-thiazolyl)carbonyl]butyl]carbamate

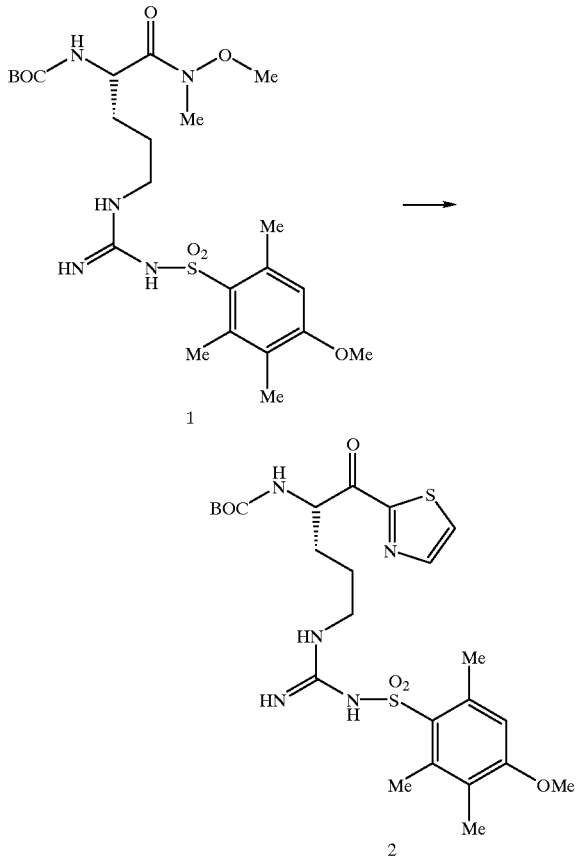

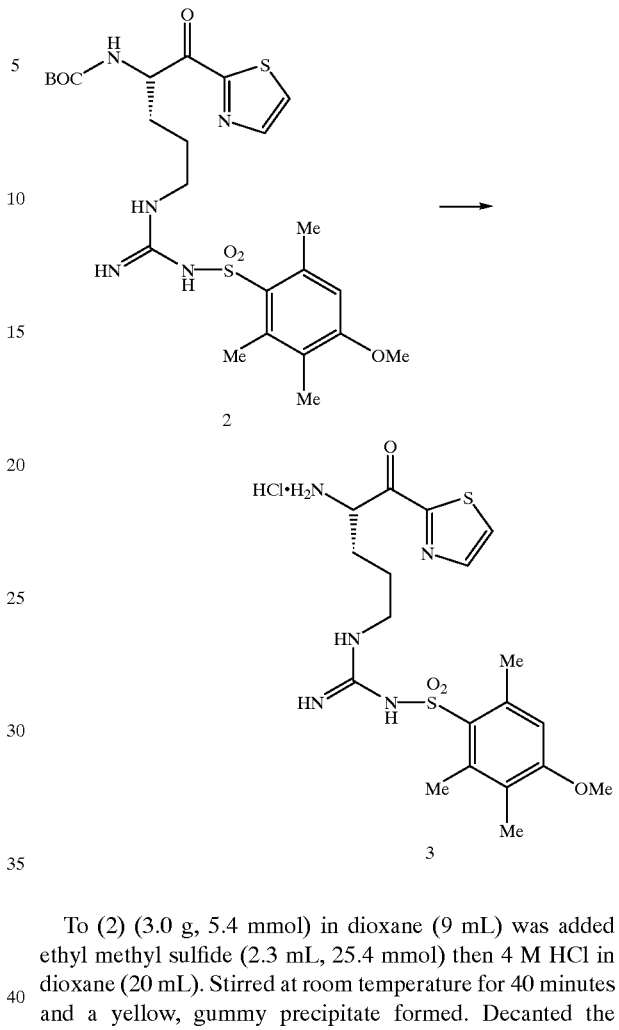

To thiazole (1.95 mL, 27.5 mmol) and TMEDA (3.8 mL, 25.2 mmol, distilled from sodium) in THF (65 mL, freshly distilled from potassium) at −78° C. was added nBuLi in hexane (13.7 mL, 24.7 mmol, 1.8 M) at a rate that raised the internal temperature to −50° C. Placed reaction flask in dry ice/acetonitrile bath to give an internal temperature of −41° C. Stirred for 25 minutes, cooled to −78° C. Added (1) (3.18 g, 6.0 mmol) in THF (33 mL) and stirred for 45 minutes. Poured reaction over a saturated aqueous ammonium chloride solution (200 mL) and shook vigorously. Extracted with ethyl acetate (2×200 mL). Combined organic phases and washed with brine (150 mL), dried with sodium sulfate, filtered, removed solvent in vacuo, purified with silica gel column eluted with 70% ethyl acetate in hexane to 100% ethyl acetate. Isolated 3.1 g (93%) of product (2) as a white foam.

1H NMR (CDCl$_3$, 300 MHz): 8.06 (1H, d, J=3.00 Hz), 7.73 (1H, d, J=3.00 Hz), 6.52 (1H, s), 6.19 (2H, bs), 5.63 (1H, d, J=8.65 Hz), 5.38–5.52 (1H, m), 3.83 (3H, s), 3.50 (3H, bs), 3.19–3.31 (1H, m), 2.68 (3H, s), 2.60 (3H, s), 2.12 (3H, s), 1.50–1.75 (4H, m), 1.42 (9H, s).
(CI MS) M+1=554, M+C$_2$H$_5$=582.

Step (c) Preparation of: (S)-N-[[[4-amino-5-oxo-5-(2-thiazolyl)pentyl]amino]iminomethyl]-4-methoxy-2,3,6-trimethyl-benzenesulfonamide To (2) (3.0 g, 5.4 mmol) in dioxane (9 mL) was added ethyl methyl sulfide (2.3 mL, 25.4 mmol) then 4 M HCl in dioxane (20 mL). Stirred at room temperature for 40 minutes and a yellow, gummy precipitate formed. Decanted the supernatant. Added ethyl acetate (40 mL) and stirred the gummy precipitate to change it to a fine granular precipitate. Isolated precipitate by filtration and washed thoroughly with ethyl acetate (150 mL) to give 3.0 g of product (3).

[1] NMR (d$_6$DMSO, 400 MHz): 8.61 (3H, bs), 8.42 (2H, d, J=3.13), 8.26 (2H, d, J=3.13), 7.03 (1H, bs), 6.67 (1H, s), 6.50 (1H, bs), 4.95–5.05 (1H, m), 3.57 (3H, s), 3.00–3.10 (2H, m), 2.56 (3H, s), 2.47 (3H, s), 1.99 (3H, s), 1.97–2.03 (1H, m), 1.82–1.90 (1H, m), 1.40–1.60 (2H, m).

(ES MS) M+1=454. [a$_D$]=+13.45°, (C=2.52, MeOH).

EXAMPLE 2

(S)-N-[[[4-amino-5-oxo-5-(2-thiazolyl)pentyl]amino]iminomethyl]-3,4-dihydro-2,2,5,7,8-pentamethyl-2H-1-benzopyran-6-ylsulfonamide Step (a) Preparation of: 1,1-dimethylethyl (S)-[4-[[imino[[(3,4-dihydro-2,2,5,7,8-pentamethyl-2H-1-benzopyran-6-yl)sulfonyl]amino]methyl]amino]-1-[(methoxymethylamino)carbonyl]butyl]carbamate BocNH—Arg(PMC)—CO$_2$H ⟶

-continued

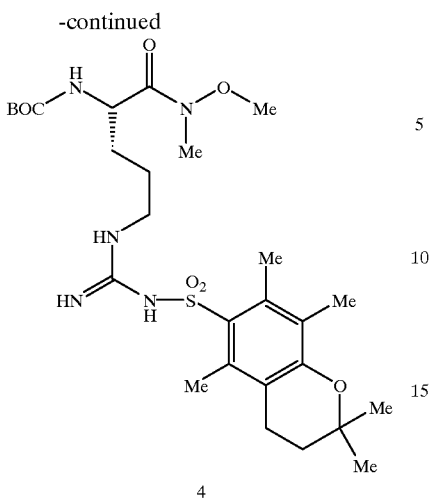

4

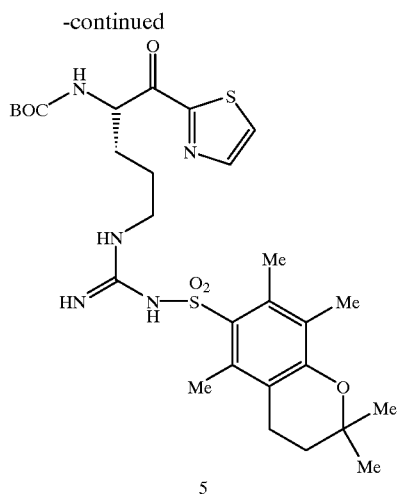

5

To Boc (L) Arg(Pmc)—OH (2.0 g, 3.7 mmol) in dichloromethane (10 mL) at 0° C. was added NMM (0.45 mL, 4.0 mmol) and IBCF (0.53 mL, 4.0 mmol). Stirred for 30 minutes. Added N,O-dimethylhydroxyl amine.HCl (0.43 g, 4.4 mmol) and NMM (0.45 g, 4.0 mmol). Stirred for 45 minutes. Diluted with ethyl acetate (100 mL), washed with 1N HCl (2×80 mL), brine (80 mL), dried MgSO$_4$ filtered, removed solvent in vacuo, purified with silica gel column eluted with 75% ethyl acetate in hexane to give 1.67 g (77%) of product (4) as a white foam.

$^1$H NMR (d$_6$DMSO, 400 MHz): 7.01 (1H,d J=8.20 Hz), 6.64 (1H, bs), 6.40 (1H, bs), 4.28–4.39 (1H, m), 3.68 (3H, s), 3.33 (3H, s), 2.97–3.10 (2H, m), 2.58 (2H, t), 2.47 (6H, s), 2.03 (3H, s), 1.77 (2H, t), 1.35–1.60 (4H, m), 1.37 (9H, s), 1.26 (6H, s).

(CI MS) M+1=584, M+C$_2$H$_5$=612.

Step (b) Preparation of: 1,1-dimethylethyl (S)-[4-[[imino[[(3,4-dihydro-2,2,5,7,8-pentamethyl-2H-1-benzopyran-6-yl)sulfonyl]amino]methyl-]amino]-1- [(2-thiazolyl)carbonyl]butyl]carbamate

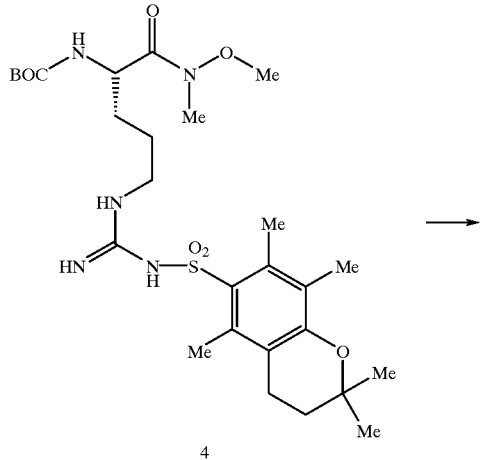

4

To thiazole (0.84 g, 11.8 mmol) and TMEDA (1.66 mL, 11.0 mmol) in THF (30 mL) at −78° C. was added nBuLi in hexane (5.4 mL, 2.0 M, 10.8 mmol). Raised temperature to −41° C., stirred for 25 minutes, cooled to at −78° C., added (4) (1.53 g, 2.62 mmol) in THF (15 mL). Stirred for 45 minutes. Quenched with saturated aqueous NH$_4$Cl (500 mL). Extracted with ethyl acetate (2×300 mL). Washed organic phase with brine (180 mL), dried with sodium sulfate, filtered, removed solvent in vacuo. Purified with silica gel column eluted with 75% ethyl acetate in hexane to 100% ethyl acetate to give 1.5 g (94%) of product (5) as a white foam.

$^1$H NMR (d$_6$DMSO, 400 MHz): 8.27 (1H, d, J=3.14 Hz), 8.18 (1H, d, J=3.14 Hz), 7.39 (1H, d, J=7.23 Hz), 6.64 (1H, bs), 6.38 (1H, bs), 5.05–5.12 (1H, m), 2.99–3.08 (2H, m), 2.57 (2H, t), 2.44 (6H, s), 2.02 (3H, s), 1.77 (2H, t), 1.42–1.58 (2H, m), 1.36 (9H, s), 1.26 (6H, s), 1.1–1.8 (2H, m).

(CI MS) M+=1 608.

Step (c) Preparation of: (S)-N-[[[4-amino-5-oxo-5-(2-thiazolyl)pentyl]amino]iminomethyl]-3,4-dihydro-2,2,5,7,8-pentamethyl-2H-1-benzopyran-6-ylsulfonamide

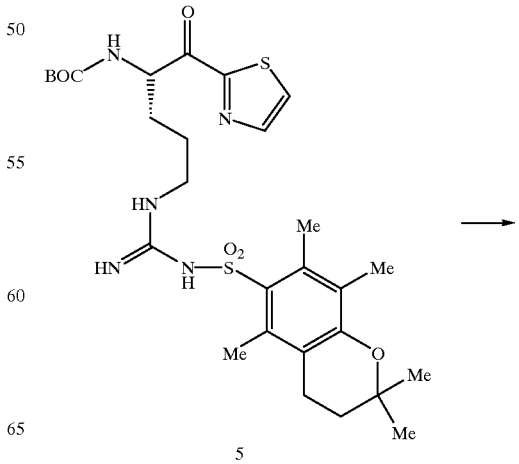

5

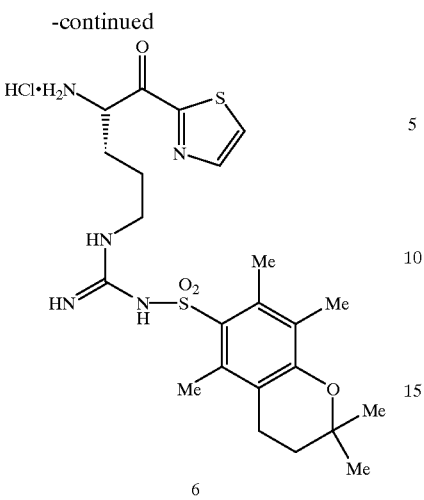

6

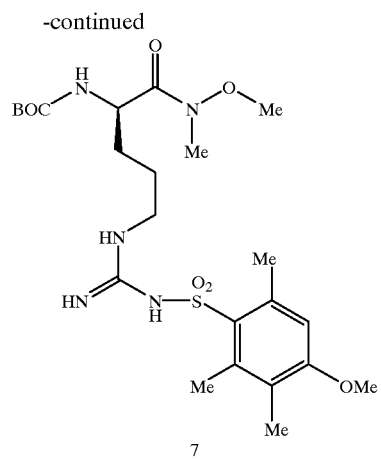

7

To (5) (0.4 g, 0.66 mmol) in dioxane (1 mL) was added ethyl methyl sulfide (0.8 g, 10 mmol) then 4 M HCl in dioxane (3 mL). Stirred at room temperature for 15 minutes. Removed solvent in vacuo. Triturated with diethyl ether (80 mL) to give 0.35 g of a yellow powder (6).

$^1$H NMR (d$_6$DMSO, 400 MHz): 8.56 (3H, bs), 8.41 (1H, d, J=3.13 Hz), 8.27 (1H, d, J=3.13 Hz), 6.90 (1H, bs), 6.45 (1H, bs), 4.95–5.05 (1H, m), 3.0–3.1 (2H, m), 2.57 (2H, t), 2.43 (6H, s), 2.02 (3H, s), 1.80–1.95 (2H, m), 1.78 (2H, t), 1.42–1.58 (2H, m), 1.26 (6H, s).

(ES MS) M+=1 507.

[a$_D$=+12.23°, (C=2.51, MeOH).

EXAMPLE 3

(R)-N-[[[4-amino-5-oxo-5-(2-thiazolyl)pentyl]amino]iminomethyl]-4-methoxy-2,3,6-trimethyl-benzenesulfonamide Step (a) Preparation of: 1,1-dimethylethyl (R)-[4-[[imino[[(4-methoxy-2,3,6-trimethylphenyl)sulfonyl]amino]methyl]amino]-1-[(methoxy-methylamino)carbonyl]butyl] carbamate

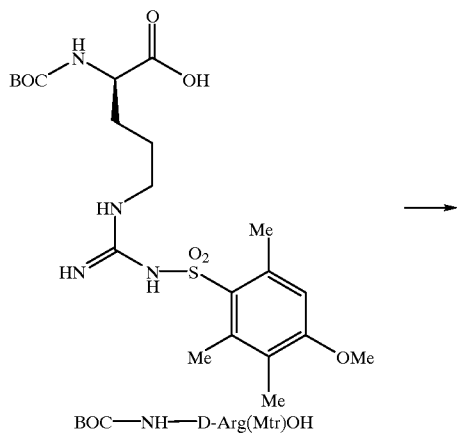

BOC—NH—D-Arg(Mtr)OH

To Boc-NH-D-Arg(Mtr)OH (5 g, 10.3 mmol) in dichloromethane (25 mL) at –10° C. was added NMM (1.2 mL, 10.8 mmol), then IBCF (1.4 mL, 10.8 mmol). Stirred for 25 minutes then added N,O-dimethylhydroxyl amine HCl (1.1 g, 11.4 mmol) and NMM (1.25 mL, 11.4 mmol) and stirred at room temperature for 1 hour. Diluted with ethyl acetate (150 mL), washed with 1N HCl (2×100 mL), brine (100 mL), dried with sodium sulfate, filtered, removed solvent, purified with silica gel column eluted with 65% ethyl acetate in hexane to 100% ethyl acetate to give 4.1 g (75%) of product (7) as a white foam.

$^1$H NMR (CDCl$_3$, 400 MHz): 6.53 (1H, s), 6.38 (1H, bs), 6.10 (1H, bs), 5.47 (1H, d, J=7.23 Hz), 4.65–4.73 (1H, m), 3.83 (3H, s), 3.73 (3H, s), 3.40–3.45 (1H, m), 3.20 (3H, s), 3.15 (1H, bs), 2.71 (3H, s), 2.63 (3H, s), 2.13 (3H, s), 1.50–1.75 (4H, m), 1.42 (9H, s).

Step (b) Preparation of: 1,1-dimethylethyl (R)-[4-[[imino[(4-methoxy-2,3,6-trimethylphenyl)sulfonyl]amino]methyl]amino]-1-(2-thiazolyl)carbonyl]butyl]carbamate

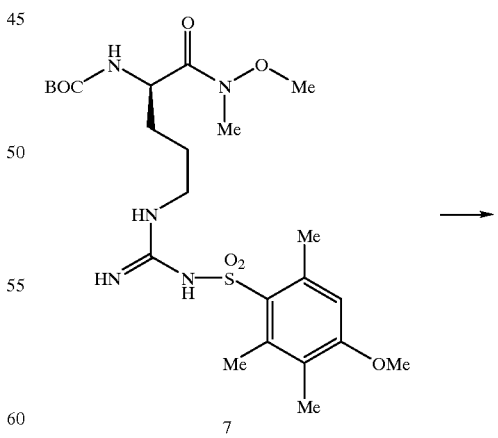

7

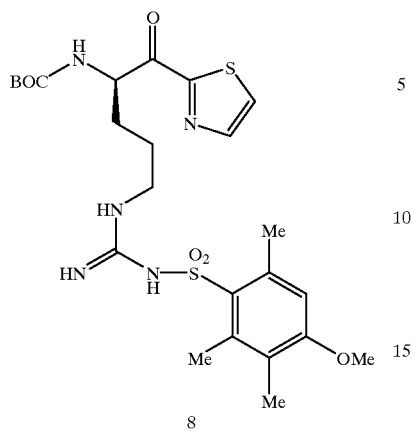

8

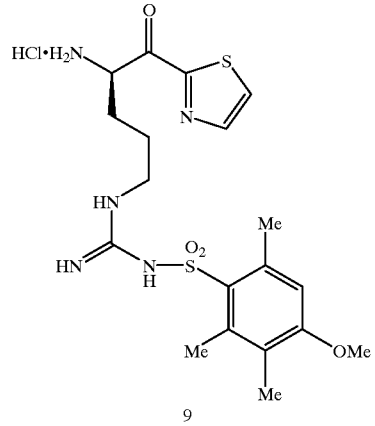

9

To thiazole (1.24 mL, 17.4 mmol) and TMEDA (2.5 mL, 16.3 mmol) in THF (43 mL) at −78° C. was added nBuLi in hexane (8.9 mL, 1.78 M, 15.9 mmol). Raised temperature to −41° C., stirred for 25 minutes, cooled to at −78° C., added (7) (2.05 g, 3.88 mmol) in THF (21 mL). Stirred for 60 minutes. Quenched with saturated aqueous NH$_4$Cl (250 mL). Extracted with ethyl acetate (2×200 mL). Washed organic phase with brine (100 mL), dried with sodium sulfate, filtered, removed solvent in vacuo. Purified with silica gel column eluted with 75% ethyl acetate in hexane to give 1.3 g (61%) of product (8) as a white foam.

$^1$H NMR (CDCl$_3$, 300 MHz): 8.07 (1H, d, J=3.00 Hz), 7.74 (1H, d, J=3.00 Hz), 6.53 (1H, s), 6.33 (2H, bs), 6.28 (2H, bs), 5.58–5.63 (1H, m), 5.40–5.50 (1H, m), 3.83 (3H, s), 3.48–3.60 (1H, m), 3.20–3.35 (1H, m), 2.70 (3H, s), 2.61 (3H, s), 2.13 (3H, s), 1.65–1.75 (2H, m), 1.55–1.65 (2H, m), 1.43 (9H, s).

Step (c) Preparation of: (R)-N-[[[4-amino-5-oxo-5-(2-thiazolyl)pentyl]amino]iminomethyl]-4-methoxy-2,3,6-trimethyl-benzenesulfonamide

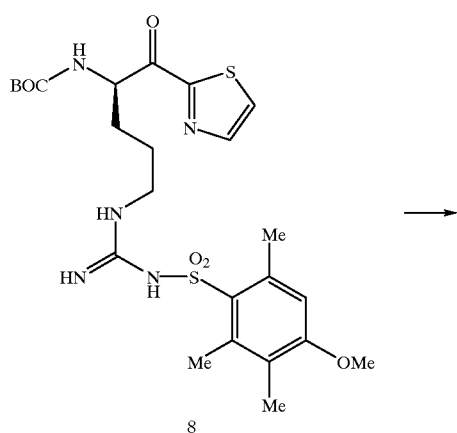

8

To (8) (1.0 g, 1.8 mmol) in dioxane (7 mL) was added ethyl methyl sulfide (1 mL, 11.0 mmol) then 4 M HCl in dioxane (7 mL). Stirred at room temperature for 30 minutes. A yellow precipitate formed. Decanted supernatant. Triturated precipitate with ethyl acetate (100 mL) and diethyl ether (3×100 mL) to give 0.9 g of a yellow powder (9).

$^1$H NMR (d$_6$DMSO, 400 MHz): 8.68 (1H, bs), 8.41 (1H, d, J=2.89 Hz), 8.26 (1H, d, J=3.14 Hz), 7.15 (1H, bs), 6.68 (1H, s), 6.55 (1H, bs), 4.95–5.05 (1H, m), 3.80 (3H, s), 3.0–3.1 (2H, m), 2.56 (3H, s), 2.47 (3H, s), 2.05 (3H, s), 1.95–2.05 (1H, m), 1.85–1.95 (1H, m), 1.40–1.57 (2H, m).

(APCI MS) M+1=454, 2M+1=907.

[a$_D$=−13.62°, (C=2.51, MeOH).

EXAMPLE 4

(S)-2,2,5,7,8-Pentamethyl-chroman-6-sulfonic acid (5-amino-6-oxo-6-thiazol-2-yl-hexyl)-amide Step (a) Preparation of: (S)-[5-tert-Butoxycarbonylamino-5-(methoxy-methyl-carbamoyl)-pentyl]carbamic acid benzyl ester

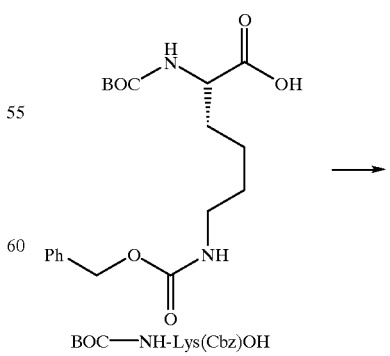

BOC—NH-Lys(Cbz)OH

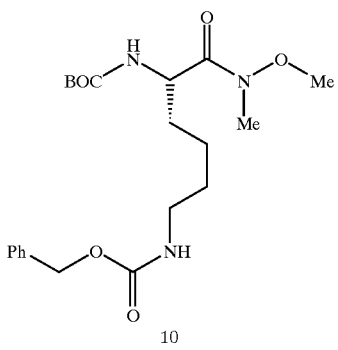

10

See also Brady S F, et al., *Biorg. Med. Chem.,* 3 (8),1063–78 (1995).

To Boc (L) Lys (Z)—OH (5.0 g, 13.7 mmol) in dichloromethane (25 mL) at −10° C. was added NMM (1.7 mL, 14.4 mmol), then IBCF (1.95 mL, 14.4 mmol). Stirred for 15 minutes then added N,O-dimethylhydroxyl amine HCl (1.6 g, 15.0 mmol) and NMM (1.8 mL, 15.0 mmol) and stirred at room temperature for 1 hour. Diluted with ethyl acetate (180 mL), washed with 1N HCl (2×100 mL), brine (100 mL), dried with sodium sulfate, filtered, removed solvent, purified with silica gel column eluted with 65% ethyl acetate in hexane to give 5.0 g (87%) of product (10) as a glass.

$^1$H NMR (CDCl$_3$, 400 MHz): 7.30–7.36 (5H, m), 5.19–5.25 (1H, m), 5.09 (2H, s), 4.87 (1H, bs), 4.66 (1H, bs), 3.76 (3H, s), 3.20 (3H, s), 3.17–3.22 (2H, bs), 1.60–1.80 (1H, m), 1.42–1.63 (5H, m), 1.42 (9H, s).

(CI MS) M+=1 424.

Step (b) Preparation of: (S)-[5-Amino-1-(methoxy-methyl-carbamoyl)-pentyl]carbamic acid tert-butyl ester

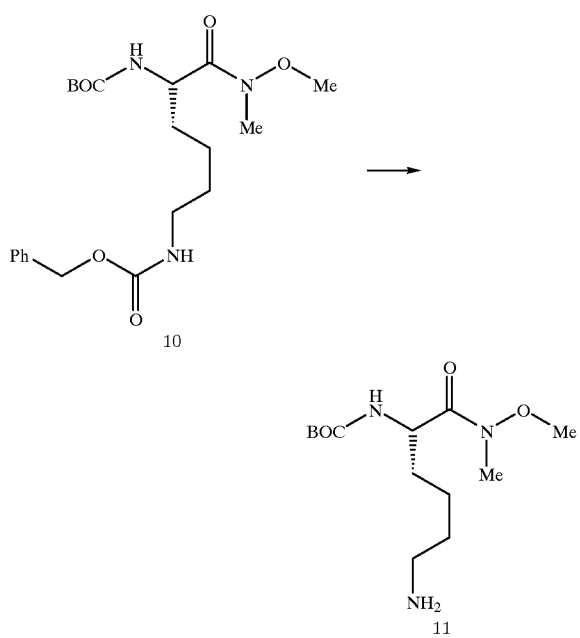

To (10) (5.0 g, 11.8 mmol) in ethanol (50 mL, degassed) was added 10% Pd/C (1.0 g) and then stirred under hydrogen balloon for 18 hours. Filtered through celite. Removed solvent. Dissolved in dichloromethane (50 mL), filtered through a small pad of silica gel, washed silica with 1% to 10% methanol in chloroform, removed solvent in vacuo to give 2.75 g (80%) of product (11) as a glass.

$^1$H NMR (CDCl$_3$, 400 MHz): 5.2 (1H, d), 4.70–4.85 (1H, m), 3.78 (3H, s), 3.21 (3H, s), 2.70 (2H, t), 1.78–1.84 (3H, m), 1.71–1.80 (1H, m), 1.45–1.60 (2H, m), 1.44 (9H, s).

(CI MS) M+1=290.

Step (c) Preparation of: (S)-[1-(Methoxy-methyl-carbamoyl)-5-(2,2,5,7,8-pentamethyl-chroman-6-sulfonylamino)-pentyl]-carbamic acid tert-butyl ester

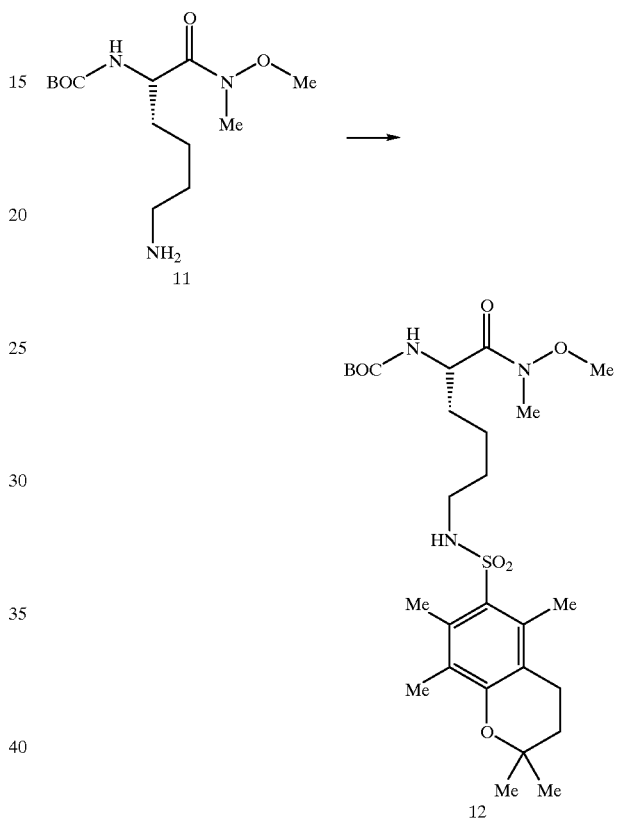

To (11) (0.4 g, 1.38 mmol) and Pmc-Cl (0.42 g, 1.38 mmol) was added THF (4 mL) and DIEA (0.24 mL, 1.38 mmol). Stirred at room temperature for 4 hours. Diluted with ethyl acetate (120 mL), washed with 1N HCl (80 mL), brine (80 mL), dried with MgSO$_4$, filtered, removed solvent in vacuo, purified with silica gel column eluted with 45% ethyl acetate in hexane to give 0.7 g (91%) of product (12).

$^1$H NMR (CDCl$_3$, 400 MHz): 5.17 (1H, d, J=8.92 Hz), 4.63 (1H, bs), 4.40–4.50 (1H, m), 3.75 (3H, s), 3.19 (3H, s), 2.89 (2H, q), 2.66 (2H, t), 2.55 (3H, s), 2.54 (3H, s), 2.05 (3H, s), 1.83 (2H, t), 1.60–1.70 (1H, m), 1.40–1.55 (3H, m), 1.43 (9H, s), 1.33–1.43 (2H, m), 1.33 (6H, s).

(CI MS) M+1=555.

Step (c) Preparation of: (S)-[5-(2,2,5,7,8-Pentamethyl-chroman-6-sulfonylamino)-1-(thiazole-2-carbonyl)-pentyl]-carbamic acid tert-butyl ester

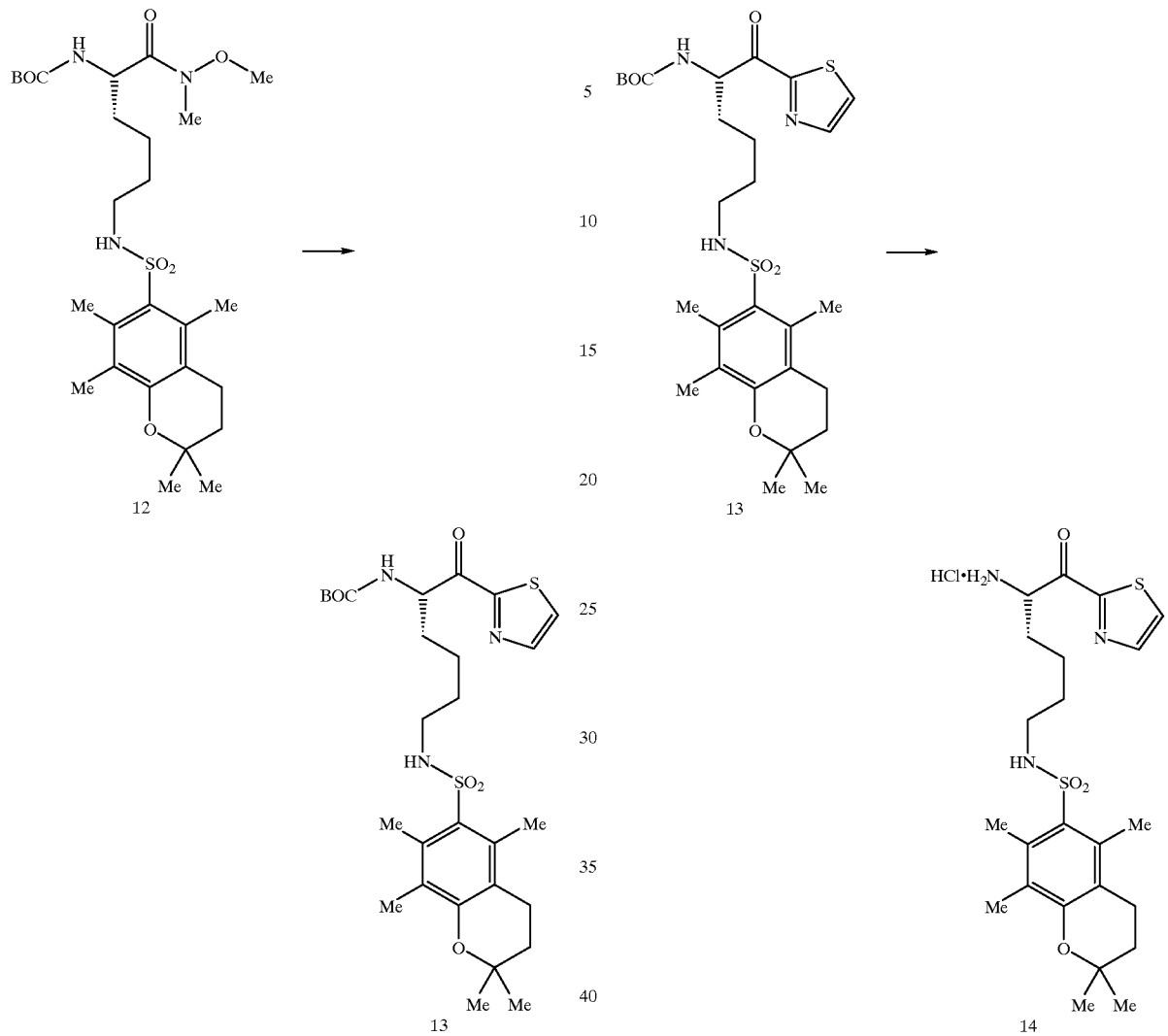

To thiazole (0.3 mL, 4.2 mmol) and TMEDA (0.55 mL, 3.6 mmol) in THF (12.5 mL) at −78° C. was added nBuLi in hexane (1.8 mL, 1.94 M, 3.5 mmol). Raised temperature to −41° C., stirred for 25 minutes, cooled to at −78° C., added (12) (0.63 g, 1.14 mmol) in THF (6 mL). Stirred for 45 minutes. Quenched with saturated aqueous NH$_4$Cl (120 mL). Extracted with ethyl acetate (2×90 mL), dried with MgSO$_4$, filtered, removed solvent in vacuo. Purified with silica gel column eluted with 35% ethyl acetate in hexane to give 0.55 g (84%) of product (13).

$^1$H NMR (CDCl$_3$, 400 MHz): 8.04 (1H, d, J=3.13), 7.71 (1H, d, J=2.89), 5.35–5.43 (2H, m), 4.45–4.55 (1H, m), 2.87 (2H, q), 2.65 (2H, t), 2.54 (3H, s), 2.53 (3H, s), 2.13 (3H, s), 1.90–2.00 (1H, m), 1.43–1.65 (6H, m), 1.43 (9H, s), 1.32 (6H, s).

(CI MS) M+1=579.

Step (d) Preparation of: (S)-2,2,5,7,8-Pentamethyl-chroman-6-sulfonic acid (5-amino-6-oxo-6-thiazol-2-yl-hexyl)-amide To (13) (0.47 g, 0.82 mmol) in dioxane (5 mL) was added ethyl methyl sulfide (0.5 mL, 5.5 mmol) and 4 M HCl in dioxane (5 mL). Stirred at room temperature for 1 hour. Added more 4 M HCl in dioxane (5 mL). Stirred for 15 minutes more. Removed solvent in vacuo. Triturated product with ethyl acetate (2×50 mL) and diethyl ether (2×50 mL) to give 0.35 g of a yellow powder (14).

$^1$H NMR (d$_6$DMSO, 400 MHz): 8.55 (2H, bs), 8.41 (1H, d, J=3.04Hz), 8.25 (1H, d, J=2.89), 7.23 (1H, t), 4.95–5.00 (1H, m), 2.70–2.80 (2H, m), 2.60 (2H, t), 2.41 (6H, s), 2.04 (3H, s), 1.81–1.97 (2H, m), 1.78 (2H, t), 1.30–1.41 (4H, m), 1.27 (6H, s).

(CI MS) M+1=480.

EXAMPLE 5

(S)-N-[[[3-amino-4-(5,6-dihydro-4H-cyclopentathiazol-2-yl)-4-oxobutyl]amino]iminomethyl]-2,2,5,7,8-pentamethyl-2H-1-benzopyran-6-sulfonamide Step (a) Preparation of: 2-Chloro-5,6-dihydro-4H-cyclopentathiazole 2-Amino-5,6-dihydro-
4-cyclopentathiazole → 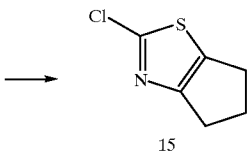

15

To cupric chloride (2.65 g, 19.7 mmol) and tert butyl nitrite (3 mL, 24.6 mmol) in acetonitrile (65 mL) was added 2-amino-5,6-dihydro-4-cyclopentathiazole (2.3 g, 16.4 mmol, free amine prepared via methylene chloride extraction of a basic solution of corresponding HCl salt) over 15 minutes. Stirred at room temperature for 2 hours, then at 65° C. for 1 hour. Filtered. Poured filtrate over 6N HCl (200 mL) and extracted with diethyl ether (300 mL). Dried with sodium sulfate, filtered, removed solvent in vacuo. Kugelrohr distilled on high vacuum pump at 95° C. to give 1.0 g (38%) of product (15) as a clear oil.

$^1$H NMR (CDCl$_3$, 400 MHz): 2.87 –2.96 (2H, m), 2.80–2.85 (2H, m), 2.41–2.54 (2H, m).

(CI MS) M+1=160.

Step (b) Preparation of: 5,6-dihydro-4H-cyclopentathiazole

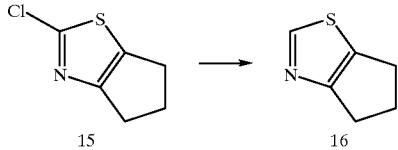

To (15) (0.5 g, 3.1 mmol) in acetic acid (16.5 ml) at reflux was added zinc dust (0.48 g, 7.3 mmol). Refluxed for 3 hours. Poured over diethyl ether (120 mL) and saturated aqueous sodium bicarbonate (120 mL). Washed diethyl ether phase with brine (80 mL), dried with sodium sulfate, filtered, removed solvent to give 0.2 g (51%) of product (16).

$^1$H NMR (CDCl$_3$, 400 MHz): 8.64 (1H, s), 2.86–2.94 (4H, m), 2.50–2.60 (2H, m).

(CI MS) M+=1 126, M(NH$_3$)=142.

Step (c) Preparation of: 1.1-dimethylethyl (S)-[1-[(2-benzothiazolyl)carbonyl]-4-[[imino[[(3,4-dihydro-2,2,5,7,8-pentamethyl-2H-1-benzopyran-6-yl)sulfonyl]amino]methyl]amino]butyl]carbamate

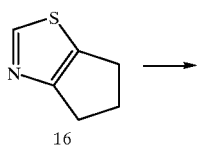 →

-continued

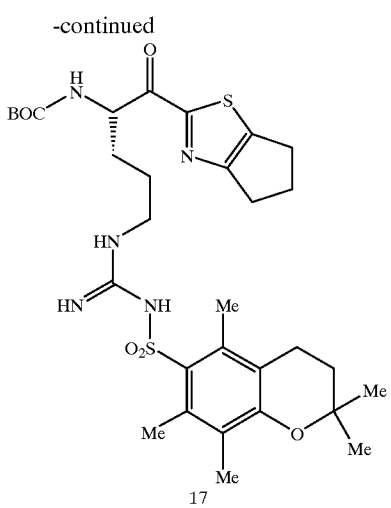

To (16) (0.63 g, 5.0 mmol) and TMEDA (0.7 mL, 4.7 mmol) in THF (10 mL) at −78° C. was added nBuLi in hexane (2.6 mL, 1.79 M, 4.6 mmol). Raised temperature to −41° C., stirred for 25 minutes, cooled to at −78° C., added (4) (Example 2, Step (a)) (0.65 g, 1.1 mmol) in THF (5 mL). Raised temperature to 0° C. Stirred for 90 minutes. Quenched with saturated aqueous NH$_4$Cl (120 mL). Extracted with ethyl acetate (2×80 mL), washed organic phase with brine (80 mL), dried with sodium sulfate, filtered, removed solvent in vacuo. Purified with silica gel column eluted with 75% ethyl acetate in hexane to give 0.52 g (72%) of product (17).

$^1$H NMR (CDCl$_3$, 400 MHz): 6.30 (1H, bs), 6.15 (2H, bs), 5.63 (1H, d, J=7.47 Hz), 5.38 (1H, t), 3.50–3.60 (1H, m), 3.20–3.30 (1H, m), 3.02 (2H, t), 2.89–2.98 (2H, m), 2.63 (2H, t), 2.57 (3H, s), 2.56 (3H, s), 2.52–2.55 (2H, m), 2.10 (3H, s), 1.80 (2H, t), 1.55–1.80 (4H, m), 1.42 (9H, s), 1.30 (6H, s).

(CI MS) M+=1 648.

Step (d) Preparation of: (S)-N-[[[3-amino-4-(5,6-dihydro-4H-cyclopentathiazol-2-yl)-4-oxobutyl]amino]iminomethyl]-2,2,5,7,8-pentamethyl-2H-1-benzopyran-6-sulfonamide

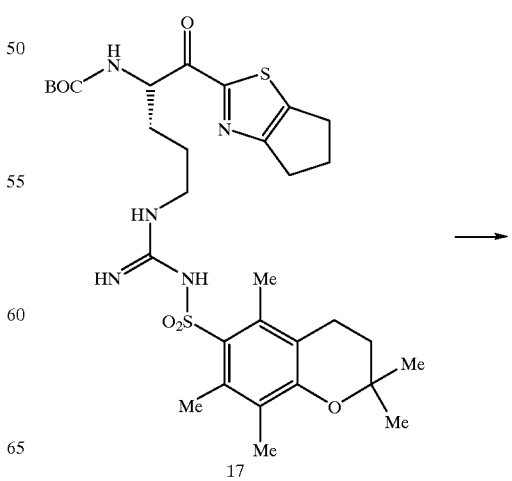

-continued

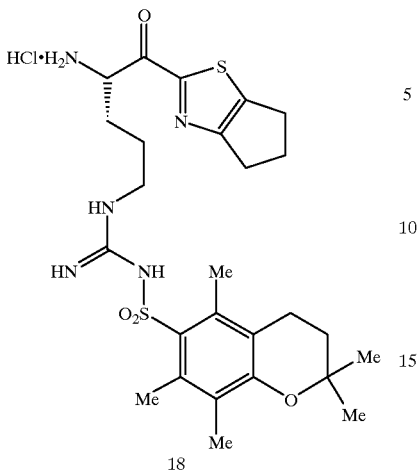

18

To (17) (0.44 g, 0.68 mmol) in dioxane (2 mL) was added ethyl methyl sulfide (0.4 mL, 4.4 mmol) and 4 M HCl in dioxane (3 mL). Stirred at room temperature for 40 minutes. Removed solvent in vacuo. Triturated with ethyl acetate (3×50 mL) to give 0.43 g of a yellow-brown powder (18).

$^1$H NMR (d$_6$DMSO, 400 MHz): 8.57 (2H, bs), 6.98 (1H, bs), 6.49 (1H, bs), 5.19 (3H, bs), 4.92–4.94 (1H, m), 3.01–3.10 (4H, m), 2.88 (2H, t), 2.57 (2H, t), 2.43 (6H, s), 2.02 (3H, s), 1.83–2.00 (2H, m), 1.76 (2H, t), 1.37–1.56 (2H, m), 1.26 (6H, s).

(APCI MS) M+1=548.7.

EXAMPLE 6

(S)-N-[[[4-amino-5-(1-methyl-1H-imidazol-2-yl)-5-oxopentyl]amino]iminomethyl]-4-methoxy-2,3,6-trimethylbenzenesulfonamide monohydrochloride Step (a) Preparation of: 1,1-dimethylethyl (S)-[4-[[imino[[(4-methoxy-2,3,6-trimethylphenyl)-sulfonyl]amino] methyl]amino]-1-[(1-methyl-1H-imidazol-2-yl)carbonyl] butyl]carbamate

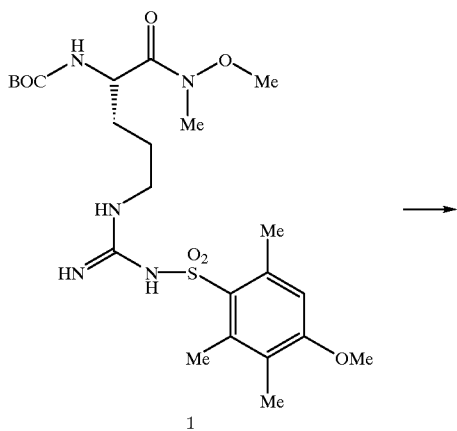

-continued

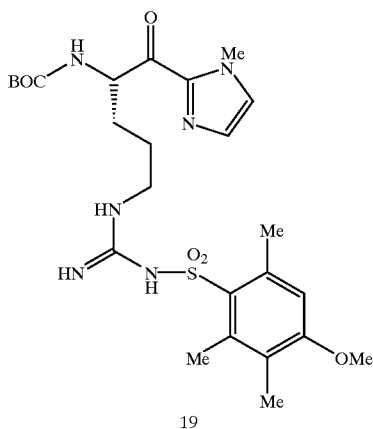

19

To N-methylimidazole (1.38 mL, 17.4 mmol) in THF (40 mL) at −78° C. was added n-BuLi in hexane (9.9 mL, 15.46 mmol, 1.56 M) titrated as described in *J. Org. Chem.,* 509 (1989) at a rate that raised the internal temperature to −50° C. The reaction flask was placed in a dry ice/acetonitrile bath to give an internal temperature of −45° C. The reaction mixture stirred for 55 minutes, then cooled to −78° C. N,O-dimethylamide (1) (2.0 g, 3.77 mmol) in THF (20 mL) was added to the reaction mixture. The internal temperature rose to −55° C. during the addition of (1) (Example 1, Step (a)). Once the addition was complete the reaction mixture was stirred for 1 hour. It was then poured over a saturated ammonium chloride solution and shook vigorously. The reaction mixture was extracted with ethyl acetate several times and the combined organic phases were washed with brine, dried with sodium sulfate, filtered, and the solvent was removed in vacuo. The product was purified on a silica gel column eluted with 2% ethanol/ethyl acetate to yield 0.98 g (49%) of the desired product (19).

NMR (DMSO-d$_6$): 7.47 (1H, s), 7.09 (1H, s), 7.04 (1H, d, J=8.03 Hz), 6.60 (1H, s), 6.30 (2H, m), 5.05 (1H, m), 3.83 (3H, s), 3.72 (3H, s), 2.94 (2H, m), 2.5 (3H, s), 2.4 (3H, s), 1.97 (3H, S) , 1.38 (4H, m) , 1.29 (9H, s).

(APCI MS) M+1=551.5.

Step (b) Preparation of: (S)-N-[[[4-amino-5-(1-methyl-1H-imidazol-2-yl)-5-oxopentyl]amino]iminomethyl]-4-methoxy-2,3,6-trimethylbenzenesulfonamide monohydrochloride

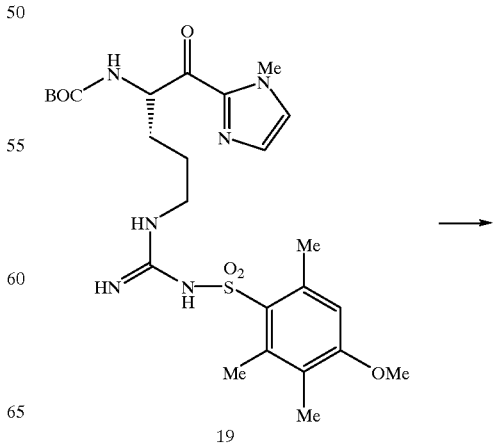

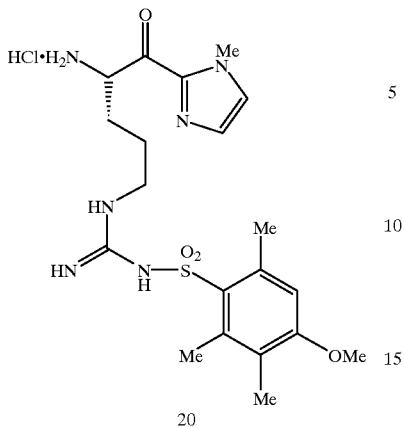

To (19) (0.46 g, 0.835 mmol) in dioxane (13 mL) was added ethyl methyl sulfide (0.35 mL) then 4 M HCl in dioxane (3 mL). The reaction mixture stirred at room temperature 1 hour and 15 minutes. The supernatant was decanted and the residue triturated with ethyl acetate, filtered, and rinsed thoroughly to yield 0.49 g of the desired product (20).

NMR (DMSO-$d_6$, $D_2O$): 7.54 (1H, s), 7.16 (1H, s), 6.59 (1H, s), 4.82 (1H, t), 3.86 (3H, s), 3.70 (3H, s), 2.99 (2H, m), 2.47 (3H, s), 2.37 (3H, s), 1.95 (3H, s), 1.78 (2H, m), 1.37 (2H, m).

(ES MS) M+1=451.5.

EXAMPLE 7

[S-(R*,R*)]-N-{[3-(2-Amino-3-oxo-3-thiazol-2-yl-propyl)-piperidin-1-yl]-imino-methyl}-4-methoxy-2,3,6-trimethyl-benzenesulfonamide hydrochloride Step (a) Preparation of: (S)-[1-(Methoxy-methyl-carbamoyl)-2-pyridin-3-yl-ethyl]-carbamic acid tert-butyl ester

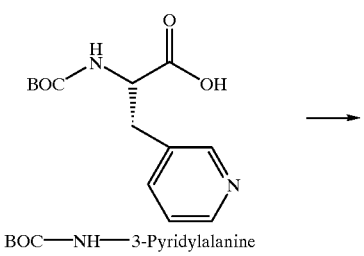

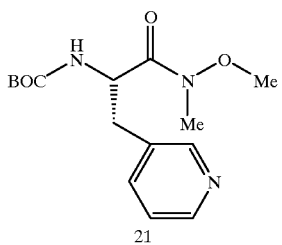

To BOC-NH-3-pyridylalanine (10.5 g, 39.5 mmol) in methylene chloride (106 mL) was added BOP reagent (18.3 g, 41.48 mmol) and DIEA (7.56 mL, 43.45 mmol). The reaction mixture stirred at room temperature for 20 minutes. To the reaction mixture was added N,O-dimethylhydroxylamine hydrochloride (3.85 g, 39.5 mmol) followed by DIEA (7.56 mL). The reaction mixture stirred 4 hours and the solvents removed in vacuo. The residue was dissolved in ethyl acetate and washed with 1N NaOH (3×25 mL), water (2×25 mL) and brine (1×50 mL), dried over sodium sulfate, filtered, and the solvents removed in vacuo. The product was crystallized form ethyl acetate/hexane to yield 5.67 g of product. The filtrate was chromatographed on silica gel eluted with 80% ethyl acetate/hexane to 100% ethyl acetate to yield 4.4 g of product. Total yield 10.07 g (82%) of the desired product (21).

$^1$H NMR (DMSO-$d_6$): 8.37 (2H, m), 7.59 (1H, d, J=7.81 Hz), 7.24 (2H, m), 4.49 (1H, m), 3.68 (3H, s), 3.05 (3H, s), 2.82 (1H, JAB=13.67 Hz, JAX=4.15 Hz), 2.68 (1H, JAB=13.67 Hz, JBX=10.36 Hz), 1.23 (9H, s).

(APCI MS) M+1=310.5.

Step (b) Preparation of: [1-(Methoxy-methyl-carbamoyl)-2-piperidin-3-yl-ethyl]-carbamic acid tert-butyl ester

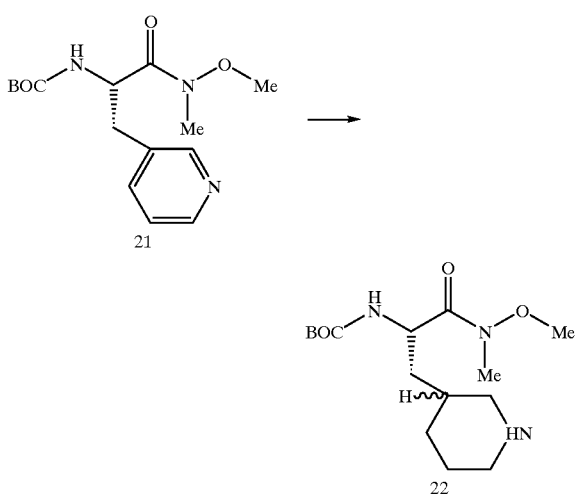

To (21) (4.4 g, 14.2 mmol) in acetic acid (100 mL) was added $PtO_2$ (0.44 g) and hydrogen gas in a Parr reactor. The reaction was complete in 23 hours. The catalyst was filtered, and the reaction mixture concentrated in vacuo. The product was dissolved in water and lyophilized to yield 5.9 g of the desired product as a sticky oil (22).

$^1$H NMR (DMSO): 7.05–7.02 (1H, d), 5.2 (1H, br), 4.36–4.30 (1H, m), 3.67 (3H, s), 3.03 (3H, s), 2.93 (3H, m), 2.50 (1H, m), 2.29 (1H, m), 1.61 (3H, m), 1.32 (2H, m), 1.31 (9H, s), 1.0 (1H, m).

(APCI MS) M+1=316.

Step (c) Preparation of: [2-(1-carbamimidoylpiperidin-3-yl)-1-(methoxy-methyl-carbamoyl)-ethyl]-carbamic acid tert-butyl ester

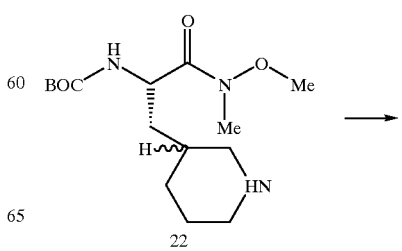

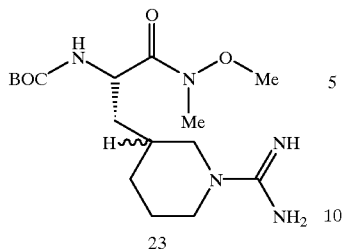

23

To (22) (6.75 g, 17.9 mmol) in DMF (9 mL) was added 1H-pyrazole-1-carboxamidine hydrochloride (2.6 g, 17.9 mmol) followed by DIEA (6.25 mL, 35 mmol). The reaction mixture stirred 4 hours at room temperature and the solvents removed in vacuo. The product was triturated with diethyl ether several times and the diethyl ether layer decanted. The product (23) was not purified but used as is in the subsequent reaction.

(APCI MS) M+1=358.6.

Step (d) Preparation of: [S-(R*,S*)]-[2-{1-[Imino-(4-methoxy-2,3,6-trimethyl-benzenesulfonyl-amino)-methyl]-piperidin-3-yl}-1-(methoxy-methyl-carbamoyl)-ethyl]-carbamic acid tert-butyl ester(24-R) and [S-(R*,R*)]-[2-{1-[Imino-(4-methoxy-2,3,6-trimethyl-benzenesulfonylamino)-methyl]-piperidin-3-yl}-1-(methoxy-methyl-carbamoyl)-ethyl]-carbamic acid tert-butyl ester(24-S)

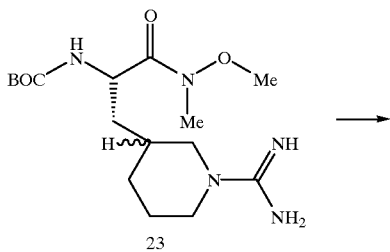

23

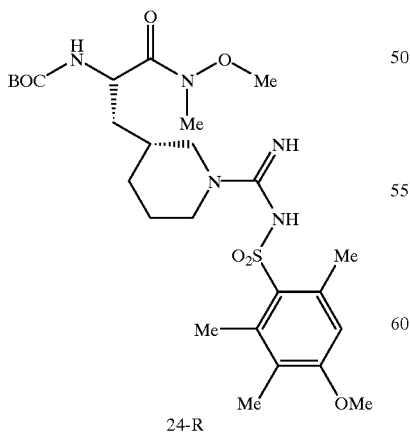

24-R

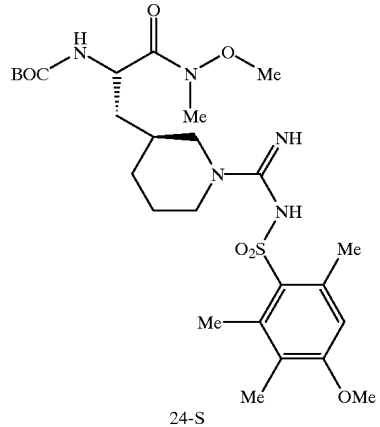

24-S

To (23) (0.56 g, 1.56 mmol) in acetone (6.8 mL) at 0° C. was added 4N NaOH (1.7 mL) and 4-methyloxy-2,3,6-trimethylbenzenesulfonyl chloride (0.679 g, 2.73 mmol) in acetone (1.7 mL). The reaction mixture stirred at 0° C. for 2.5 hours. Added 10% citric acid until the pH=6.0. The solvents were removed in vacuo. The residue was extracted with ethyl acetate several times and the combined organic phases were washed with brine, dried over magnesium sulfate, filtered, and the solvents removed in vacuo. The product was purified on silica gel eluted with ethyl acetate to yield 396 mg (24-R) and 211 mg (24-S).

(24-R) $^1$H NMR (DMSO-$d_6$,$D_2O$): 6.60 (1H, s), 4.31 (1H, m), 3.97 (1H, m), 3.98 (1H, m), 3.78 (1H, m), 3.70 (3H, s), 3.59 (3H, s), 2.99 (3H, s), 2.70 (1H, m), 2.50 (3H, s), 2.44 (3H, s), 2.42 (1H, m), 1.97 (3H, s), 1.62 (1H, m), 1.53 (1H, m) 1.28 (9H, s), 1.38–1.21 (2H, m), 1.20–1.0 (2H, m).

(24-S) $^1$H NMR (DMSO-$d_6$,$D_2O$): 6.90 (1H, d), 6.62 (1H, s), 4.35 (1H, m), 3.71 (3H, s), 3.67 (2H, m), 3.60 (3H, s), 3.00 (3H, s), 2.83 (1H, m), 2.63 (1H, m), 2.50 (3H, s), 2.43 (3H, s), 1.98 (3H, s), 1.70 (1H, m), 1.55 (1H, m), 1.29 (9H, s), 1.45–1.0 (5H, m).

(APCI MS) M+1=570.5.

Step (e) Preparation of: [S-(R*,R*)]-(1-{1-[Imino-(4-methoxy-2,3,6-trimethyl-benzenesulfonylamino) -methyl]-piperidin-3-ylmethyl}-2-oxo-2-thiazol-2-yl-ethyl)-carbamic acid tert-butyl ester

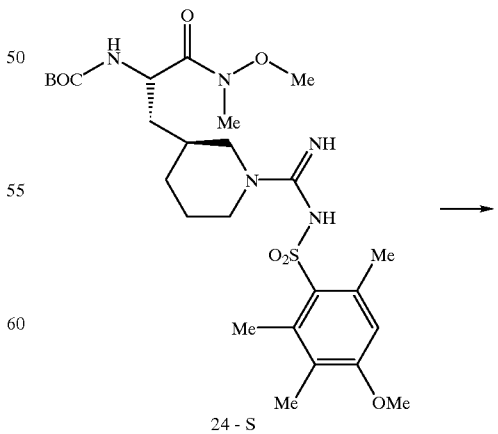

24-S

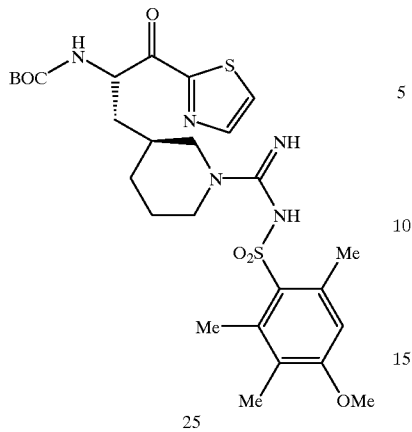

25

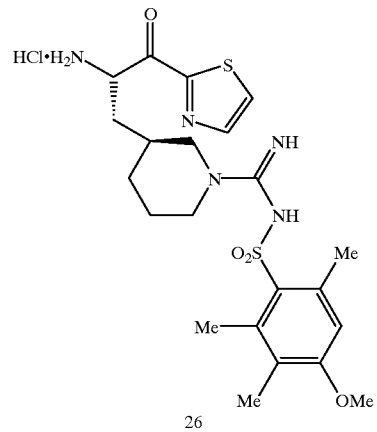

26

To thiazole (0.26 g, 2.66 mmol) and TMEDA (0.37 mL, 2.44 mmol) in THF (6.3 mL) at −78° C. was added n-BuLi in hexane (1.7 mL, 2.38 mmol, 1.4 M) at a rate that raised the internal temperature to −55° C. The reaction mixture was placed in a dry ice/acetonitrile bath to give an internal temperature of −41° C. Stirred for 25 minutes then cooled to −78° C. (24-S) (0.330 g, 0.58 mmol) in THF (3.2 mL) was added to the reaction mixture and stirred for 45 minutes. The reaction mixture was poured over saturated ammonium chloride solution, shook vigorously, and extracted several times with ethyl acetate. The combined organic phases were washed with brine and dried over sodium sulfate, filtered, and the solvent removed in vacuo. The product was purified on silica gel eluted with 70% ethyl acetate/hexanes to 100% ethyl acetate. Isolated 0.25 g (73%) of the desired product (25).

$^1$H NMR (DMSO-d$_6$): 8.21 (1H, d, J=2.93 Hz), 8.12 (1H, d, J=3.17 Hz), 7.35 (1H, d, J=7.57 Hz), 6.94 (2H, s), 6.60 (1H, s), 5.36 (1H, m), 3.76 (2H, m), 3.73 (3H, s), 2.83 (1H, m), 2.63 (1H, m), 2.50 (3H, s), 2.43 (3H, s),1.97 (3H, s), 1.81 (1H, m), 1.60 (2H, m), 1.20–1.18 (4H, m), 1.27 (9H, s).

(APCI MS) M+1=594.4.

Step (f) Preparation of: [S-(R*,R*)]-N-{[3-(2-Amino-3-oxo-3-thiazol-2-yl-propyl)-piperidin-1-yl-]-imino-methyl}-4-methoxy-2,3,6-trimethyl-benzenesulfonamide hydrochloride To (25) (0.23 g, 0.39 mmol) in dioxane (1.2 mL) was added ethyl methyl sulfide (0.18 mL) then 4 M HCl in dioxane (1.56 mL). The reaction mixture stirred at room temperature for 40 minutes. A yellow gummy precipitate formed. The supernatant was decanted and the residue triturated with ethyl acetate to yield a yellow solid. Isolate the precipitate by filtration and wash with ethyl acetate to yield 0.267 g of the desired product (26).

$^1$H NMR (DMSO-d$_6$, D$_2$O): 8.24 (1H, d, J=2.93 Hz), 8.14 (1H, d, J=2.93 Hz), 6.59 (1H, s), 4.96 (1H, m), 3.8 (2H, m), 3.49 (3H, s), 2.85 (1H, m), 2.62 (1H, m), 2.47 (3H, s), 2.40 (3H, s), 1.99 (3H, s), 1.78 (1H, m), 1.60 (2H, m), 1.22 (4H, m).

(ES MS) M+1=494.5.

EXAMPLE 8

[S-(R*,S*)]-N-{[3-(2-Amino-3-oxo-3-thiazol-2-yl-propyl)-piperidin-1-yl]-imino-methyl}-4-methoxy-2,3,6-trimethyl-benzenesulfonamide hydrochloride Step (a) Preparation of: [S-(R*,S*)]-(1-{1-[Imino-(4-methoxy-2,3,6-trimethyl-benzenesulfonylamino)-methyl-1piperidin-3-ylmethyl}-2-oxo-2-thiazol-2-yl-ethyl)-carbamic acid tert-butyl ester

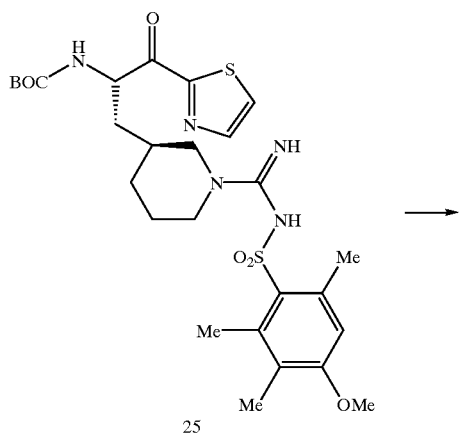

25

→

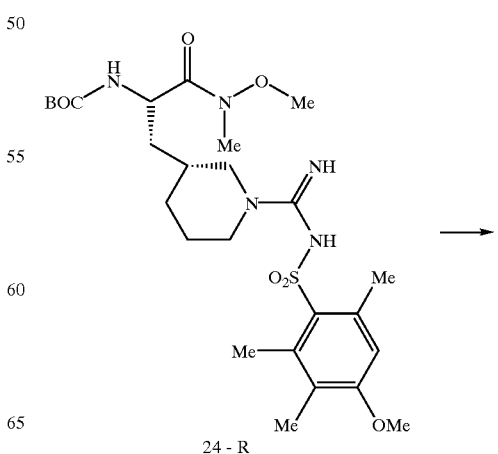

24-R

→

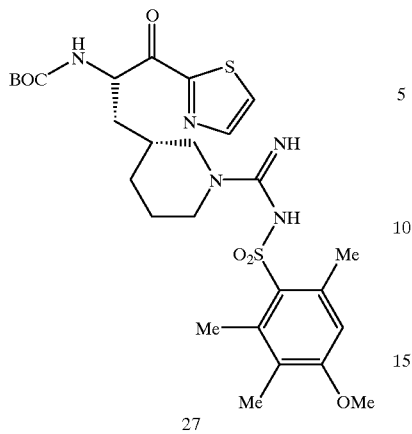

27

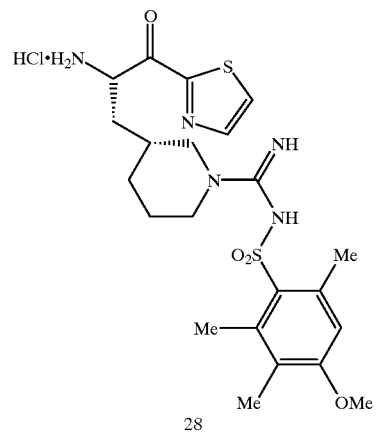

28

To thiazole (0.43 g, 5.0 mmol) and TMEDA (0.7 mL, 4.66 mmol) in THF (12 mL) at −78° C. Was added n-BuLi in hexane (2.39 mL, 4.55 mmol, 1.9 M). The reaction mixture was placed in a dry ice/acetonitrile bath to give an internal temperature of −41° C. Stirred for 20 minutes then cooled to −78° C. (24-R) (Example 7, Step (d)) (0.63 g, 1.11 mmol) in THF (11 mL) was added to the reaction mixture at a rate that maintained an internal temperature of −78° C. And stirred for 50 minutes. The reaction mixture was poured over saturated ammonium chloride solution, shook vigorously, and extracted several times with ethyl acetate. The combined organic phases were washed with brine and dried over sodium sulfate, filtered, and the solvent removed in vacuo. The product was purified on silica gel and eluted with 70% ethyl acetate/hexanes. Isolated 0.56 g (85%) of the desired product (27).

$^1$H NMR (DMSO): 8.21 (1H, d, J=2.93 Hz), 8.12 (1H, d, J=2.93 Hz), 7.52 (1H, d, J=7.08 Hz), 6.98 (2H, s), 6.62 (1H, s), 5.13 (1H, m), 4.16 (1H, m), 3.84 (1H, m), 3.74 (3H, s), 2.72 (1H, m), 2.53 (3H, s), 2.46 (3H, s), 1.99 (3H, s), 1.68 (1H, m), 1.49 (4H, m), 1.30 (9H, s), 1.22–1.01 (2H, m).

(APCI MS) M+1=594.

Step (b) Preparation of: [S-(R*,S*)]-N-{[3-(2-Amino-3-oxo-3-thiazol-2-yl-propyl)-piperidin-1-yl]-imino-methyl}-4-methoxy-2,3,6-trimethyl-benzenesulfonamide hydrochloride

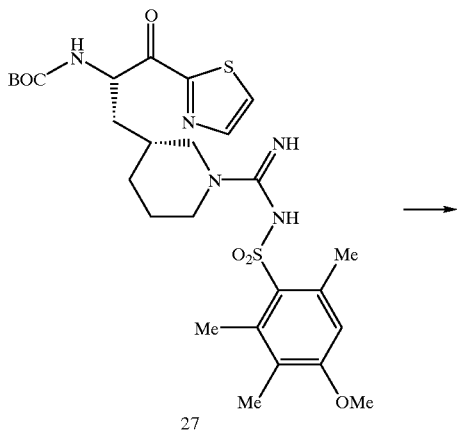

27

To (27) (0.50 g, 0.84 mmol) in dioxane (2.5 mL) was added ethyl methyl sulfide (0.35 mL) then 4 M HCl in dioxane (3.0 mL). The reaction mixture stirred at room temperature for 30 minutes. A yellow gummy precipitate formed. The supernatant was decanted and the residue triturated with ethyl acetate to yield a yellow solid. Isolate the precipitate by filtration and wash with ethyl acetate to yield 0.57 g of the desired product (28).

$^1$H NMR (DMSO-d$_6$): 8.57 (NH), 8.5 (NH), 8.44 (1H, d, J=2.93 Hz), 8.20 (1H, d, J=2.93 Hz), 7.08 (2H, NH), 6.64 (1H, s), 5.08 (1H, m), 3.93 (br, m), 3.74 (3H, s), 2.72 (1H, m), 2.63 (1H, m), 2.54 (3H, s), 1.99 (3H, s) 1.9–1.5 (5H, m), 1.2–1.0 (2H, m).

(ES MS) M+1=494.

EXAMPLE 9

(S)-N-{[4-(2-Amino-3-oxo-3-thiazol-2-yl-propyl)-piperidin-1-yl]-imino-methyl}-4-methoxy-2,3,6-trimethyl-benzenesulfonamide Step (a) Preparation of: (S)-(1-{1-[Imino-(4-methoxy-2,3,6-trimethyl-benzenesulfonylamino)-methyl-piperidin-4-ylmethyl}-2-oxo-2-thiazol-2-yl-ethyl)-carbamic acid tert-butyl ester

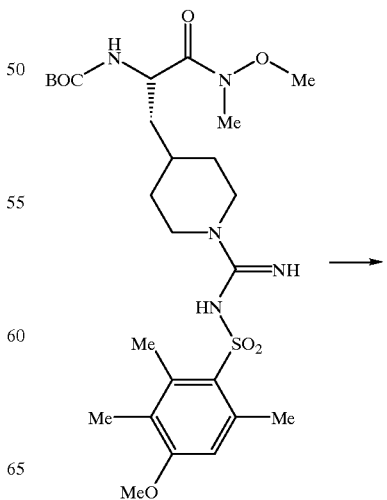

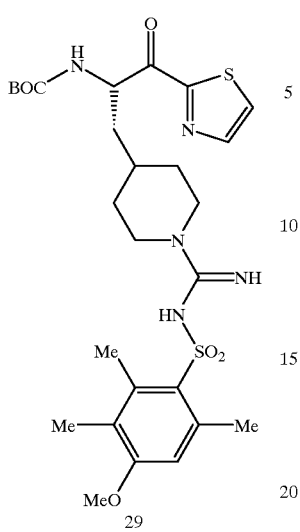

29

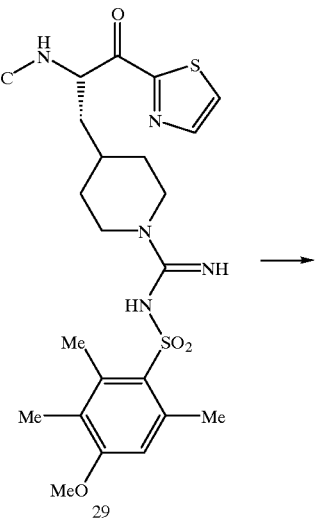

29

To thiazole (0.38 mL, 5.37 mmol) and TMEDA (0.75 mL, 14.9 mmol) in THF (12.9 mL) at −78° C. Was added n-BuLi in hexane (2.6 mL, 4.87 mmol, 1.87 M) at a rate that raised the internal temperature to −45° C. The flask was placed in a dry ice/acetonitrile bath to give an internal temperature of −45° C. The reaction mixture was stirred for 30 minutes and then cooled to −78° C. The N,O-dimethylamide, (S)-[2-{1-[Imino-(4-methoxy-2,3,6-trimethyl-benzenesulfonylamino)-methyl]-piperidin-4-yl}-1-(methoxy-methyl-carbamoyl)-ethyl]-carbamic acid tert-butyl ester prepared in a similar manner to Example 7 Steps (a)–(d), (0.68 g, 1.19 mmol) in THF (10 mL) was added. The reaction mixture was stirred 50 minutes then poured into saturated ammonium chloride solution, shook vigorously, and extracted several times with ethyl acetate. The combined organics were washed with brine, dried over sodium sulfate, filtered, and the solvent removed in vacuo. The product was purified on silica gel column eluted with 80% ethyl acetate/20% hexane to yield 0.72 g of the desired product (29).

$^1$H NMR (DMSO-$d_6$): 8.21 (1H, d, J=2.93 Hz), 8.13 (1H, d, J=2.93 Hz), 7.36 (1H, d, J=7.57 Hz), 6.97 (2H, brs), 6.63 (1H, s), 5.14 (1H, m), 3.97 (2H, m), 3.73 (3H, s), 2.71 (2H, m), 2.53 (3H, s), 2.45 (3H, s), 1.99 (3H, s), 1.8–1.4 (5H, m), 1.30 (9H, s), 1.09 (1H, m), 0.94 (1H, m).

(APCI MS) M+1=594.5.

Step (b) Preparation of: (S)-N-{[4-(2-Amino-3-oxo-3-thiazol-2-yl-propyl)-piperidin-1-yl]-imino-methyl}-4-methoxy-2,3,6-trimethyl-benzenesulfonamide

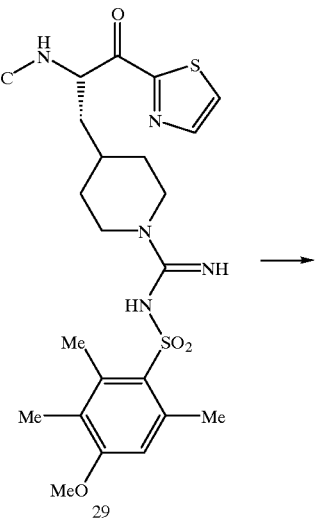

30

To (29) (0.49 g, 0.83 mmol) in dioxane (1.5 mL) was added ethyl methyl sulfide (0.35 mL) then 4 M HCl in dioxane (3.0 mL). The reaction mixture stirred at room temperature for 45 minutes and a gummy precipitate formed. The supernatant was decanted and ethyl acetate (15 mL) was added to the residue and stirred until a fine granular precipitate formed. The product was isolated by filtration and washed thoroughly with ethyl acetate to yield 0.517 g (98%) of the desired product (30).

$^1$H NMR (DMSO): 8.43 (3H, br s), 8.35 (1H, d, J=2.93 Hz), 8.21 (1H, d, J=2.93 Hz), 7.00 (2H, br s), 6.62 (1H, s), 5.01 (1H, m), 3.82 (2H, m), 3 73 (3H, s), 2.80 (1H, m), 2.57 (1H, m) 2.52 (3H, s) 2.45 (3H, s), 1.98 (3H, s), 1.80 (1H, m), 1.50 (2H, m), 1,30 (2H, m), 1.16 (2H, m).

(APCI MS) M+1=494.2.

EXAMPLE 10

(S)-N-[[[4-amino-5-(2-benzisothiazolyl)-5-oxopentyl]amino]iminomethyl]-4-methoxy-2,3,6-trimethylbenzene-sulfonamide monohydrochloride Step (a) Preparation of: 1,1-dimethylethyl (S)-[1-[(2-benzisothiazolyl)carbonyl]-4-[[imino[[(4-methoxy-2,3,6-trimethylphenyl)sulfonyl]-amino]methyl]amino]butyl] carbamate

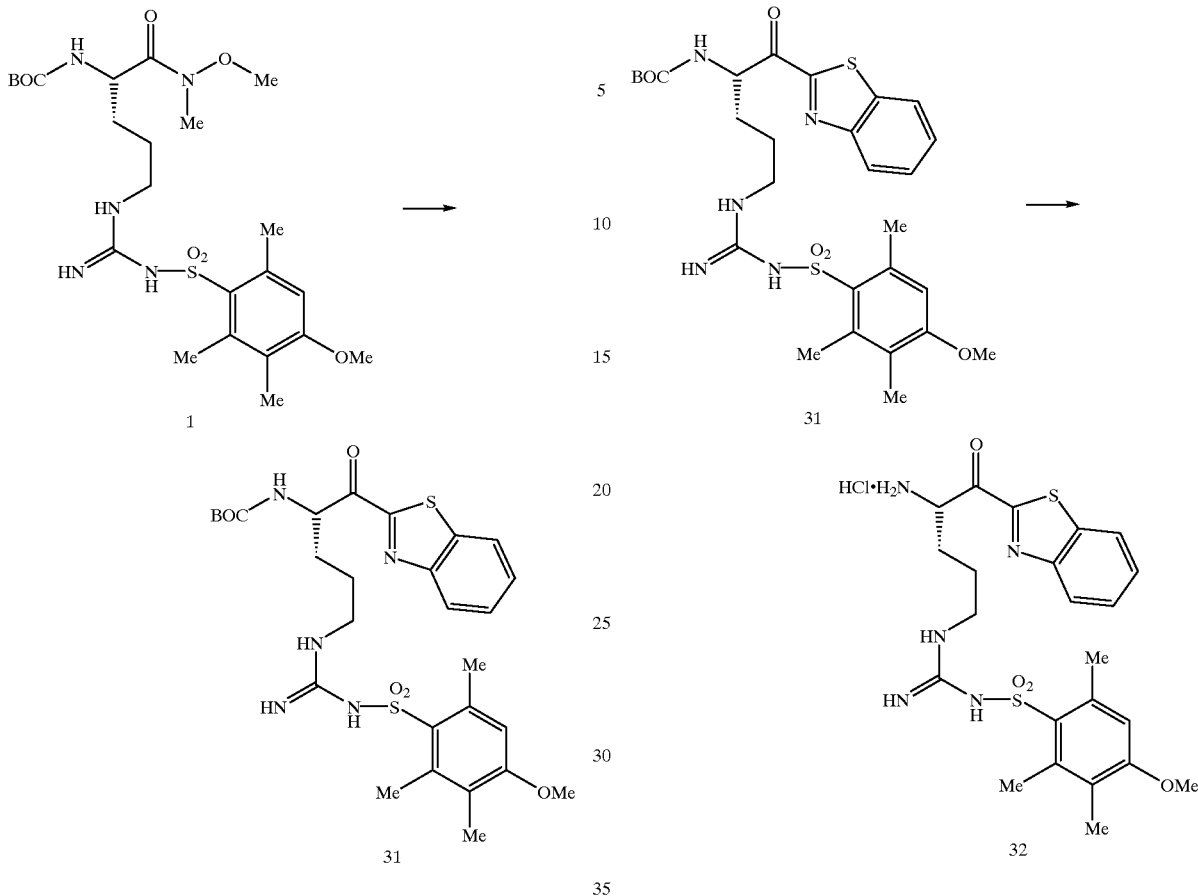

To benzothiazole (0.94 mL, 8.6 mmol) and TMEDA (1.19 mL, 7.9 mmol) in THF (20 mL) at −78° C. was added n-BuLi in hexane (3.85 mL, 7.7 mmol, 2.0 M) at a rate that raised the internal temperature to −60°C. The reaction mixture stirred for 40 minutes at −60° C. to −78°C. Added (1) (Example 1, Step (a)) (1.0 g, 1.88 mmol) in THF (10 mL) and stirred for 45 minutes [Note: internal temperature rises to −60° C. during the addition of (1)]. The reaction mixture was poured over saturated ammonium chloride solution and extracted several times with ethyl acetate. The combined organics were washed with brine, dried over sodium sulfated filtered, and the solvent was removed in vacuo. The product was purified on silica gel column eluted with 70% ethyl acetate/hexanes to yield 560 mg of the desired product (31).

$^1$H NMR (DMSO-$d_6$): 8.19 (2H, m), 7.61 (2H, m), 7.46 (1H, d, J=7.08 Hz), 6.58 (1H, s), 5.14 (1H, m), 3.72 (3H, s), 3.0 (3H, m), 2.45 (3H, s), 2.44 (3H, s), 1.94 (3H, s), 1.82 (1H, m), 1.52 (3H, m), 1.30 (9H, s)

(APCI MS) M+1=604.4.

Step (b) Preparation of: (S)-N-[[[4-amino-5-(2-benzisothiazolyl)-5-oxopentyl]amino]iminomethyl]-4-methoxy-2,3,6-trimethylbenzenesulfonamide monohydrochloride To (31) (0.56 g, 0.93 mmol) in dioxane (2.75 mL) was added ethyl methyl sulfide (0.38 mL) then 4 M HCl in dioxane (3.3 mL). Stirred at room temperature for 1 hour and a yellow gummy precipitate formed. The supernatant was decanted and the residue triturated with ethyl acetate. The precipitate was isolated by filtration and washed thoroughly with ethyl acetate to yield 348 mg of the desired product (32).

$^1$H NMR (DMSO-$d_6$): 8.47 (NH, s), 8.27 (2H, in), 8.23 (2H, m), 7.66 (NH, m), 6.57 (1H, s), 5.11 (1H, m), 3.72 (3H, s), 3.0 (2H, m), 2.45 (3H, s), 2.4 (3H, s), 1.93 (3H, s), 2.08–1.8 (2H, m), 1.58–1.40 (2H, m).

(APCI MS) M+1=504.4.

EXAMPLE 11

(S)-N-[[[4-amino-5-(2-pyridinyl)-5-oxoipentyl]amino]iminomethyl]-4-methoxy-2,3,6-trimethylbenzenesulfonamide monohydrochloride Step (a) Preparation of: 1,1-dimethylethyl (S)-[4-[[imino[[(4-methoxy-2,3,6-trimethylphenyl)sulfonyl]amino]methyl]amino]-1-[(2-pyridinyl)carbonyl]butyl]carbamate

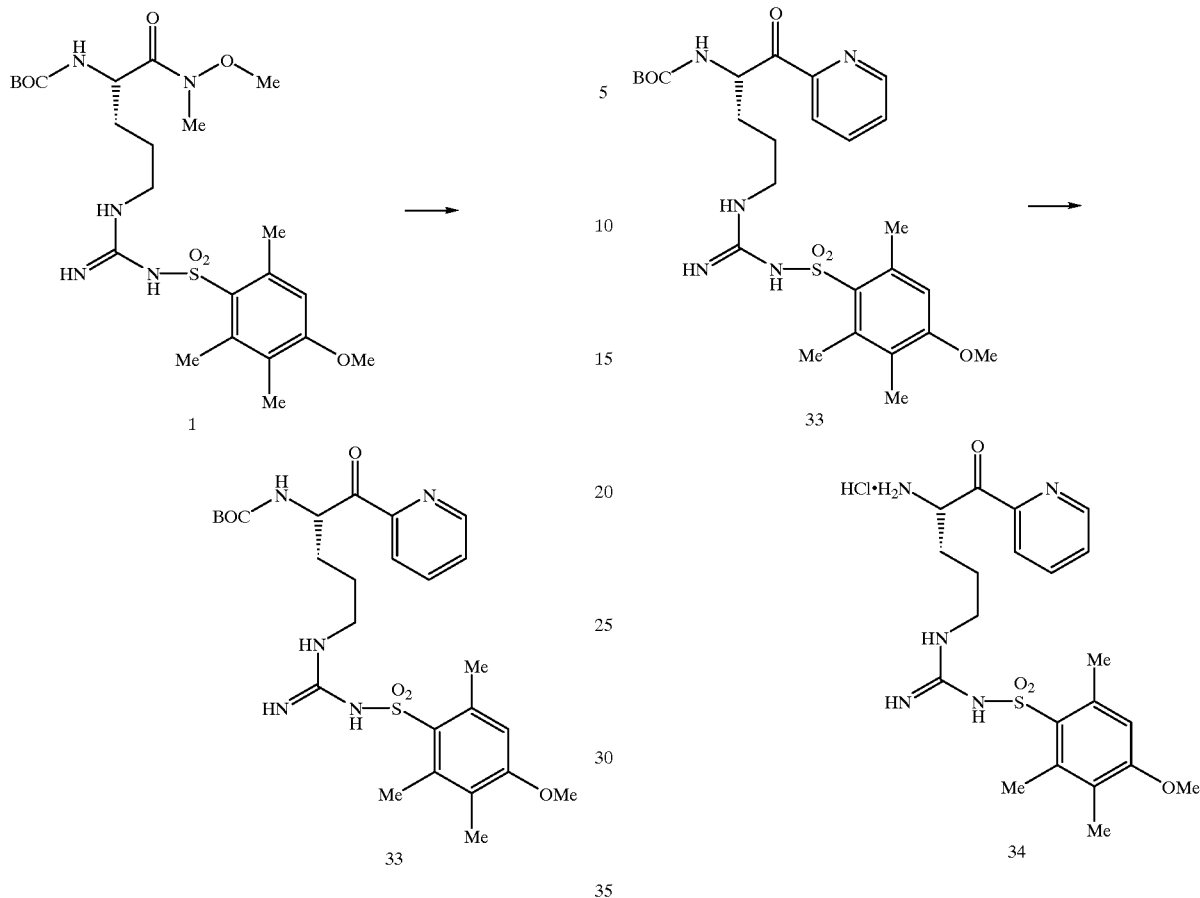

To 2-bromopyridine (0.82 mL, 8.66 mmol) in THF (10 mL) at −78° C. was added n-BuLi in hexane (5.5 mL, 7.94 mmol, 1.54 M), at a rate that kept the internal temperature at −78°C. The reaction mixture was stirred at −78° C. for 30 minutes. The N,O-dimethylamide (1) (Example 1, Step (a)) (1.0 g, 1.89 mmol) in THF (5 mL) was added to the reaction mixture and stirred for 1 hour. The reaction mixture was poured over saturated ammonium chloride solution, shook vigorously, and extracted several times with ethyl acetate. The combined organic phases were washed with brine, dried with sodium sulfate, filtered, and the solvent removed in vacuo. The product was purified on a silica gel column eluted with ethyl acetate to yield 0.62 g (63%) of the desired product (33).

$^1$H NMR (DMSO-$d_6$): 7.88 (1H, d), 7.63 (1H, m), 7.14 (1H, d, J=7.81 Hz), 6.80 (1H, br), 6.60 (1H, s), 6.30 (1H, br), 5.30 (1H, m), 3.73 (3H, s), 2.97 (2H, m), 2.51 (3H, s), 2.42 (3H, s), 1.97 (3H, s), 1.62 (1H, br), 1.40 (1H, br), 1.29 (9H, s), 0.83 (1H, s).

(CI MS) M+1=548.

Step (b) Preparation of: (S)-N-[[[4-amino-5- (2-pyridinyl)-5-oxopentyl]amino]-iminomethyl]-4-methoxy-2,3,6-trimethylbenzenesulfonamide monohydrochloride To (33) (0.3 g, 0.55 mmol) in dioxane (1.0 mL) was added ethyl methyl sulfide (0.23 mL) then 4 M HCl in dioxane (2.0 mL). Stirred at room temperature for 30 minutes. The product that precipitated was filtered, and washed thoroughly with ethyl acetate to yield 0.27 g (98%) of the desired product (34).

$^1$H NMR (DMSO-$d_6$): 8.71 (1H, d, J=4.15 Hz), 8.39 (3H, br s), 8.02 (2H, m), 7.72 (1H, m), 6.61 (1H, s), 5.16 (1H, m), 3.73 (3H, s), 2.97 (2H, m), 2.50 (3H), 2.40 (3H, s), 1.98 (3H, s), 1.88 (1H, m), 1.7 (1H, m), 1.4 (2H, m).

(CI MS) M+1=448.

EXAMPLE 12

(S)-N-[[[4-amino-5-(1-methyl-1H-benzimidazol-2-yl)-5-oxopentyl]amino]iminomethyl]-4-methoxy-2,3,6-trimethylbenzenesulfonamide monohydrochloride Step (a) Preparation of: 1,1-dimethylethyl (S)-[[imino[[(4-methoxy-2,3,6-trimethylphenyl)sulfonyl]amino]methyl]amino]-1-[(1-methyl-1H-benzimidazol-2-yl)carbonyl]butyl] carbamate

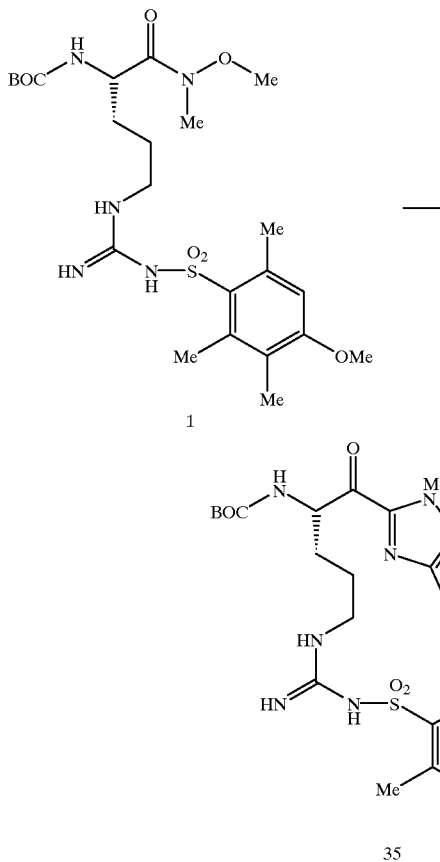

1

35

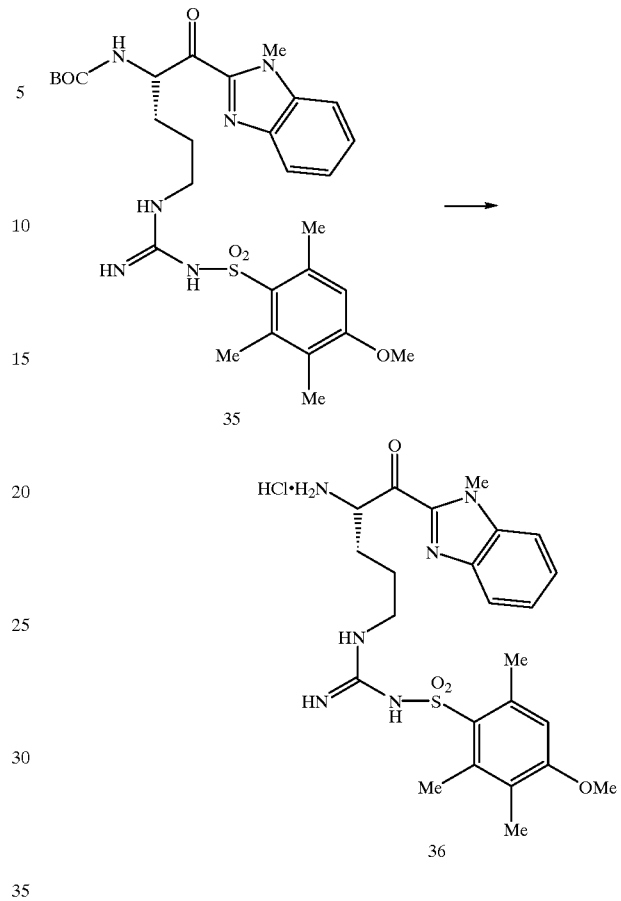

35

36

To 2-methylbenzoimidazole (2.29 g, 17.3 mmol) in THF (30 mL) at −78° C. was added n-BuLi in hexane (10.2 mL, 15.8 mmol, 1.54 M). The reaction mixture stirred for 45 minutes, then added N,O-dimethyl amide (1) (Example 1, Step (a)) (2.0 g, 3.78 mmol) in THF (20 mL) while maintaining an internal temperature of −78°C. The reaction mixture was stirred 2 hours. The reaction mixture was poured over saturated ammonium chloride solution (200 mL), shook vigorously, and then extracted with ethyl acetate. The combined organic phases were washed with brine and dried with sodium sulfate, filtered, and the solvent removed in vacuo. The product was purified on a silica gel column eluted with 80% ethyl acetate/hexane to yield 0.78 g (34%) of the desired product (35).

$^1$H NMR (DMSO-$d_6$): 7.79 (1H, d, J=8.05 Hz), 7.68 (1H, d, J=8.3 Hz), 7.31 (2H, m), 7.313 (1H, t, J1=8.3 Hz, J2=7.08 Hz), 7.29 (1H, s), 6.9 (1H, br), 6.59 (1H, s), 6.31 (1H, br), 5.24 (1H, m), 4.02 (3H, s), 3.72 (3H, s), 2.98 (2H, m), 2.50 (3H, s), 2.41 (3H, s), 1.95 (3H, s), 1.75 (2H, m), 1.48 (2H, m), 1.29 (9H, s).

(CI MS) M+1=601.

Step (b) Preparation of: (S)-N-[[[4-amino-5-(1-methyl-1H-benzimidazol-2-yl)-5-oxopentyl]amino]iminomethyl]-4-methoxy-2,3,6-trimethylbenzenesulfonamide monohydrochloride To (35) (0.24 g, 0.4 mmol) in dioxane (1.0 mL) was added ethyl methyl sulfide (0.23 mL) then 4 M HCl in dioxane (2.0 mL). The reaction mixture stirred 1 hour at room temperature. A white precipitate formed and the supernatant was decanted and ethyl acetate (45 mL) was added to the residue. The product was stirred until it became a granular precipitate. The product was isolated by filtration and washed thoroughly with ethyl acetate to yield 0.19 g (98%) of the desired product (36).

$^1$ NMR (DMSO-$d_6$): 8.47 (2H, br), 7.82 (1H, d, J=8.05 Hz), 7.75 (1H, d, J=8.54 Hz), 7.49 (1H, t, J1=7.32 Hz, J2=7.08 Hz), 7.37 (1H, t, J1=8.05 Hz, J2=7.32 Hz), 6.90 (1H, br), 6.58 (1H, s), 6.40 (1H, br), 5.12 (1H, m), 4.07 (3H, s), 3.71 (3H, s), 2.98 (2H, m), 2.45 (3H, s), 2.37 (3H, s), 1.96 (1H, m), 1.93 (3H, s), 1.84 (1H, m), 1.44 (2H, m).

(APCI MS) M+1=501.

EXAMPLE A

[6S-[6α[R*(R*)],8aα]]-2-(3-Phenyl-propionyl)-octahydropyrrolo[1,2-a]pyrazine-6-carboxylic acid [4-quanidino-1-(thiazole-2-carbonyl)-butyl]-amide trifluoroacetate To a solution of 4-oxo-2-(3-phenyl-propionyl)-octahydropyrrolo[1,2-a]pyrazine-6-carboxylic acid (0.155 g, 0.490 mmol) {HPLC retention time 7.23 minutes, eluting with a gradient of 20% acetonitrile to 76% acetonitrile in water containing 0.1% TFA over 22 minutes} in DMF (3 mL) at room temperature was added the (3)(Example 1, Step (c)) (0.309 g, 1.2 equiv.), diisopropylethylamine (0.42 mL, 4 equiv.) and then BOP-reagent (0.326 g, 1.5 equiv.). The mixture was stirred for 3 hours and then diluted with water (50 mL) and extracted with ethyl acetate (2×50 mL). The organic phase was washed with brine (50 mL), dried over MgSO$_4$ and then purified by silica gel chromatography, eluting with 95% ethylacetate/5% methanol, to afford the intermediate [6S-[6αR*(R*), 8aα]]-4-[[imino[[(4-methoxy-2,3,6-trimethylphenyl)sulfonyl]amino]methyl]amino]-1-[(2-thiazolyl)carbonyl]-butyl]octahydro-4-oxo-2-(1-oxo-3-phenylpropyl)pyrrolo-[1,2-a]pyrazine-6-carboxamide (0.260 g, 71%). To a solution of this compound (0.260 g, 0.346 mmol) in thioanisole (0.3 mL) at room temperature was added TFA (3 mL). This solution was stirred at room temperature for 2.5 hours and then evaporated in vacuo and treated with diethyl ether to precipitate a white solid. This solid was purified by reverse phase chromatography eluting with 80% acetonitrile in 20% water containing 0.1% TFA. The appropriate fractions were combined and lyophilized to afford the title compound (A) (0.102 g, 45%).

$^1$NMR (DMSO-d$_6$): 8.84 (1H, d, J=7.0 Hz), 8.28 (1H, d, J=3.1 Hz), 8.19 (d, J=2.9 Hz), 7.45 (1H, t, J=5.5 Hz), 7.25 (5H, m), 7.17 (1H, m), 5.36 (1H, m), 4.62 (1H, m), 4.45 (2H, m), 4.25 (2H, m), 3.81 (1H, d, J=17 Hz), 3.65–3.50 (1H, m), 3.47 (1H, d, J=17 Hz), 3.1 (2H, m), 2.95 (1H, m), 2.90 (2H, m), 2.85 (1H, m), 2.6–2.4 (2H, m), 2.35–2.18 (1H, m), 2.05 (1H, m), 1.95 (1H, m), 1.65 (4H, m), 1.45 (1H, m).

(ES MS) 540.

EXAMPLE B

[6S-[6α[R*(R*)],8aα]]-2-(3-Phenyl-propionyl)-octahydropyrrolo[1,2-a]pyrazine-6-carboxylic acid [1-(1-carbamimidoyl-piperidin-3-ylmethyl)-2-oxo-2-thiazol-2-yl-ethyl]-amide trifluoroacetate To (26) (Example 1, Step (f)) (0.225 g, 0.42 mmol) and 4-oxo-2-(3-phenyl-propionyl)-octahydro-pyrrolo-[1,2-a] pyrazine-6-carboxylic acid (0.124 g, 0.39 mmol) {HPLC retention time 7.23 minutes, eluting with a gradient of 20% acetonitrile to 76% acetonitrile in water containing 0.1% TFA over 22 minutes} in DMF (3.9 mL) was added BOP reagent (0.263 g, 0.595 mmol) and N-methyl morpholine (0.22 mL, 2.0 mmol). The reaction mixture was stirred at room temperature for 3.5 hours. The reaction mixture was diluted with ethyl acetate and washed with 10% citric acid, then brine, dried with sodium sulfate, filtered, and the solvent removed in vacuo. The product was purified on a silica gel column eluted with 5% methanol/ethyl acetate. Isolated 0.127 g (42%) of the desired product [6S-[6α[R*(R*)],8aα]]-N-[1-[[1-[imino[[(4-methoxy-2,3,6-trimethylphenyl)sulfonyl]amino]methyl]-3-piperidinyl] methyl]-oxo-2-(2-thiazolyl)ethyl]octahydro-4-oxo-2-(1-oxo-3-phenylpropyl)pyrrolo[1,2-a]pyrazine-6-carboxamide. To this compound (0.113 g, 0.142 mmol) and ethyl methyl sulfide (0.12 mL) at 0° C. was added TFA (1.1 mL). The reaction mixture stirred at 0° C. for 30 minutes and at room temperature for 6 hours. To the mixture was added TFA (1.0 mL) and the reaction stirred an additional 30 minutes. The TFA and ethyl methyl sulfide were removed in vacuo and the residue triturated with diethyl ether. The precipitate was isolated by filtration and washed thoroughly with diethyl ether. The product was purified by reverse phase high pressure liquid chromatography eluting with acetonitrile/water, containing 0.1% TFA, to yield 42.9 mg of the desired product (B).

NMR (DMSO-d$_6$): 8.63 (1H, d, J=7.23 Hz), 8.48 (1H, d, J=3.13 Hz), 8.19 (1H, d, J=3.13 Hz), 7.25 (8H, m), 5.45 (1H, m), 4.70 (1H, m), 4.42 (2H, m), 4.24 (1H, m), 2.98 (2H, m), 2.83–2.68(6H, m), 2.62–2.53(1H, m), 2.19 (1H, m), 2.02 (1H, m), 1.90 (1H, m) 1.88–1.44 (7H, m), 1.25 (1H, m).

MS (ES) M+1=580.

What is claimed is:

1. A compound of Formula I (D(−)) or Formula I (L(+))

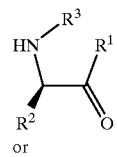

I(D(−))

or

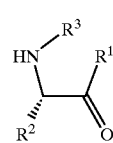

I(L(+))

wherein R$^1$ is

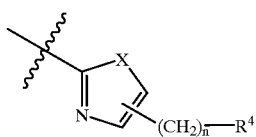

wherein X is O, or n is zero, and

R$^4$ is H,

R$^2$ is —(CH$_2$)$_q$—Y wherein Y is

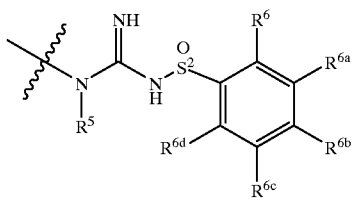

wherein R$^5$ is as defined above, and R$^6$, R$^{6a}$, R$^{6b}$, R$^{6c}$, R$^{6d}$ are the same or different and are H, alkyl, alkenyl, alkynyl, cycloalkyl, or OR$^5$ wherein R$^5$ is as defined above,

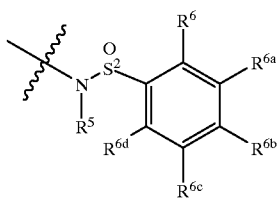

wherein R$^5$, R$^6$, R$^{6a}$, R$^{6b}$, R$^{6c}$, and R$^{6d}$ are as defined above,

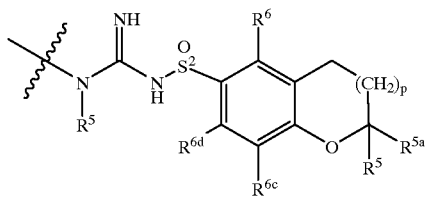

wherein p is zero or an integer of 1 to 2, and $R^5$, $R^{5a}$, $R^6$, $R^{6c}$, and $R^{6d}$ are as defined above, or

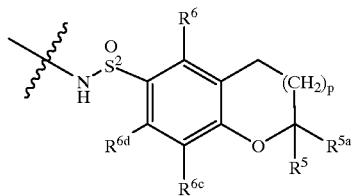

wherein p, $R^5$, $R^{5a}$, $R^6$, $R^{6c}$, and $R^{6d}$ are as defined above, and q is an integer of 3 to 6,

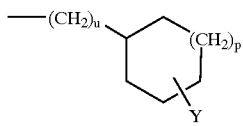

wherein u is zero or an integer of one, and p and y are as defined above,

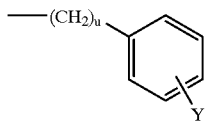

wherein u and Y are as defined above,

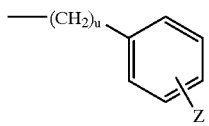

wherein Z is

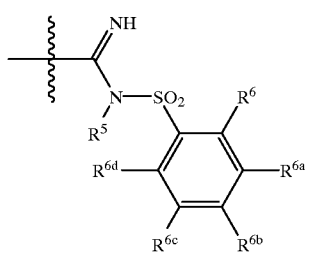

wherein $R^5$, $R^6$, $R^{6a}$, $R^{6b}$, $R^{6c}$, and $R^{6d}$ are as defined above, or

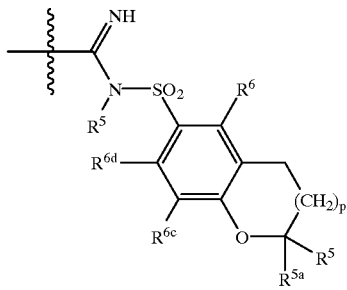

wherein p, $R^5$, $R^{5a}$, $R^6$, $R^{6c}$, and $R^{6d}$ are as defined above, and wherein u is as defined above,

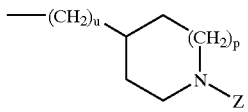

wherein u, p, and z are as defined above,

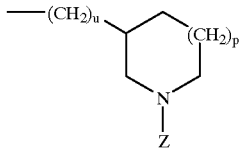

wherein u, p, and z are as defined above,

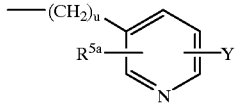

wherein u, $R^{5a}$, and Y are as defined above,

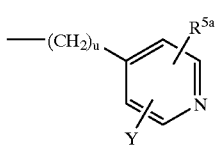

wherein u, $R^{5a}$, and Y are as defined above,

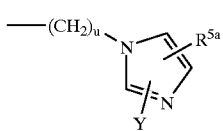

wherein u, $R^{5a}$, and Y are as defined above,

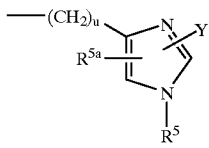

wherein u, $R^{5a}$, $R^5$ and Y are as defined above,

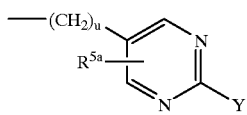

wherein u, $R^{5a}$, and Y are as defined above, or

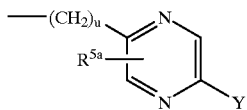

wherein u, $R^{5a}$, and Y are as defined above; and $R^3$ is H,

—$CO_2R^7$ wherein $R^7$ is alkyl,
cycloalkyl,
cycloalkylalkyl,
arylalkyl, or
aryl, or an addition salt thereof.

2. A compound according to claim 1 wherein $R^2$ is —$(CH_2)_3$—Y wherein Y is

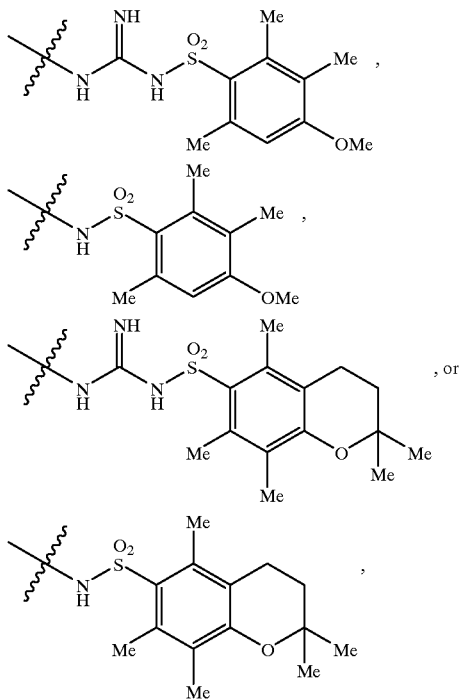

—$(CH_2)_4$—Y wherein Y is as defined above,

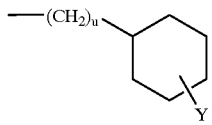

wherein u is zero or an integer of one and Y is as defined above,

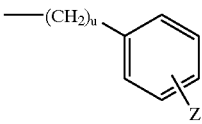

wherein Z is

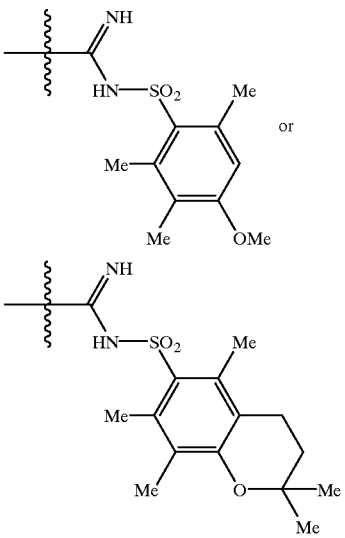

wherein u is as defined above,

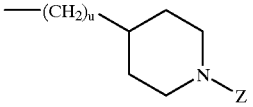

wherein u and Z are as defined above, or

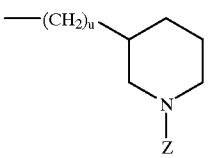

wherein u and Z are as defined above;

$R^3$ is H, or

—$CO_2R^7$ wherein $R^7$ is alkyl.

3. A compound of Formula I (D(−)) or Formula I (L(+)):

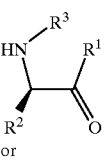

I(D(−))

or

-continued
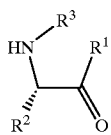
wherein R¹ is
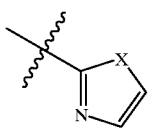
wherein X is O, or
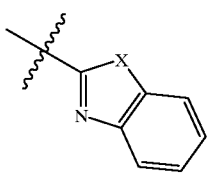
R² is —(CH$_2$)$_3$—Y wherein Y is
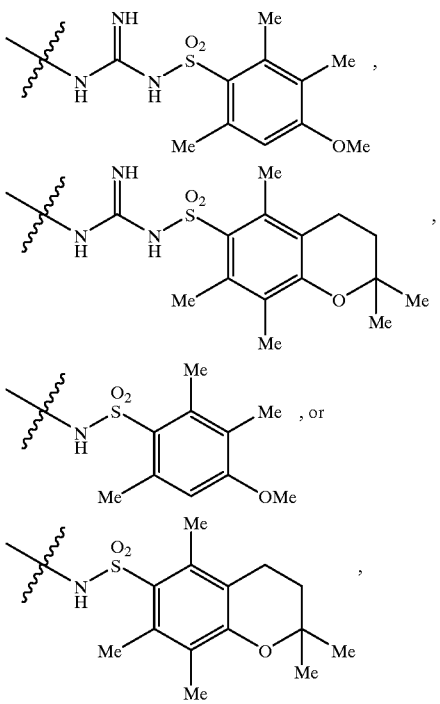
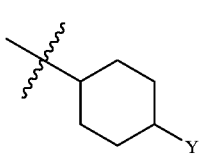
wherein Y is as defined above,
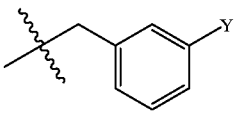
wherein Y is as defined above,
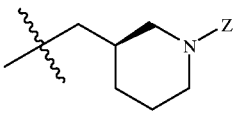
wherein Z is
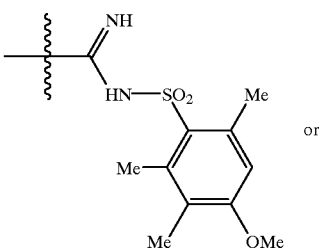
or
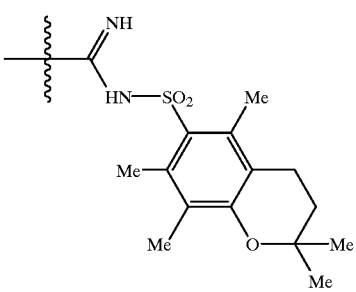
wherein Z is as defined above,
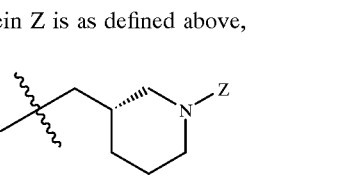
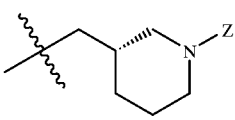
and R³ is CO$_2$t-Bu.
4. A compound of Formula I (D(−)) or Formula I (L+)):
I(D(-))
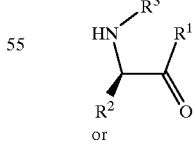
or
I(L(+))
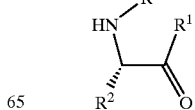

wherein R¹ is

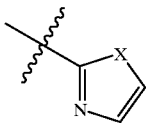

wherein X is O or S,

R² is —(CH₂)₃—Y wherein Y is

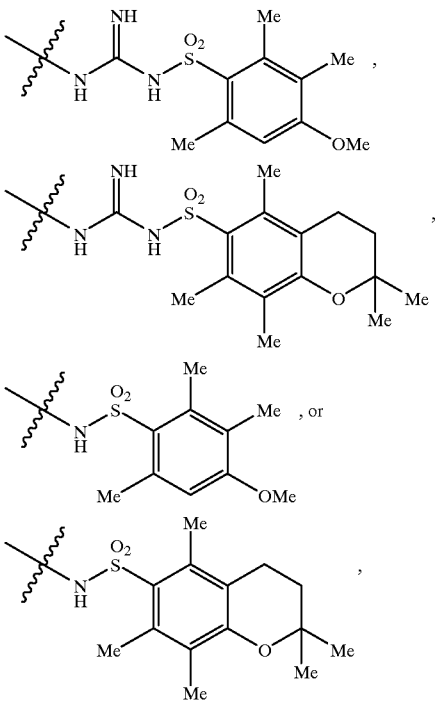

wherein Y is as defined above,

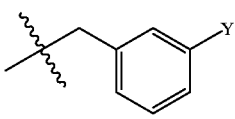

wherein Y is as defined above,

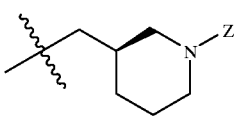

wherein Z is

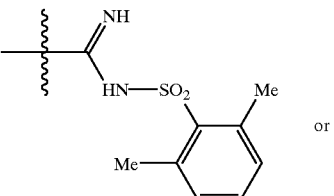

or

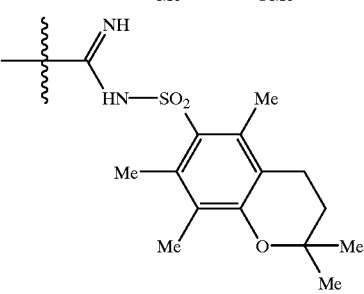

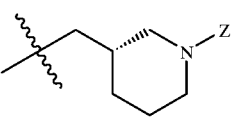

wherein Z is as defined above, and R³ is H; or an addition salt thereof.

5. A compound selected from the group consisting of:
(S)-N-((4-amino-5-oxo-5-(2-thiazolyl)-pentyl)amino) iminomethyl)-4-methoxy-2,3,6-trimethyl-benzenesulfonamide,
(S)-N-((4-amino-5-oxo-5-(2-thiazolyl-pentyl)amino) imonomethyl)-3,4-dihydro-2,2,5,7,8-pentamethyl-2H-1-benzopyran-6-sulfonamide,
(R)-N-((4-amino-5-oxo-5-(2-thiazolyl)-pentyl)amino) iminomethyl)-4-methoxy-2,3,6-trimethyl-benzenesulfonamide,
(S-(R*,R*))-N-{(3-(2-amino-3-oxo-3-thiazol-2-yl-propyl)-piperidin-1-yl)-imino-methyl}-4-methoxy-2,3,6-trimethyl-benzenesulfonamide,
(S-(R*,R*))-N-{(3-(2-amino-3-oxo-3-thiazol-2-yl-propyl)-piperidin-1-yl)-imino-methyl}-3,4-dihydro-2,2,5,7,8-pentamethyl-2H-1-benzopyran-6-sulfonamide,
(S)-N-{(3-(2-amino-3-oxo-3-thiazol-2-yl-propyl)-phenyl)-imino-methyl}-4-methoxy-2,3,6-trimethyl-benzenesulfonamide,
(S)-N-{(3-(2-amino-3-oxo-3-thiazol-2-yl-propyl)-phenyl)-imino-methyl}-3,4-dihydro-2,2,5,7,8-pentamethyl-2H-1-benzopyran-6-sulfonamide,
(R-(R*,R*))-N-{3-(2-amino-3-oxo-3-thiazol-2-yl-propyl)-piperidin-1-yl)-imino-methyl}-4-methoxy-2,3,6-trimethyl-benzenesulfonamide,
(R-(R*,R*))-N-{3-(2-amino-3-oxo-3-thiazol-2-yl-propyl)-piperidin-1-yl)-imino-methyl}-3,4-dihydro-2,2,5,7,8-pentamethyl-2H-1-benzopyran-6-sulfonamide,
(R)-N-{(3-(2-amino-3-oxo-3-thiazol-2-yl-propyl)-phenyl)-imino-methyl}-4-methoxy-2,3,6-trimethyl-benzenesulfonamide, and
(R)-N-{(3-(2-amino-3-oxo-3-thiazol-2-yl-propyl)-phenyl)-imino-methyl}-3,4-dihydro-2,2,5,7,8-pentamethyl-2H-1-benzopyran-6-sulfonamide.

* * * * *

UNITED STATES PATENT AND TRADEMARK OFFICE
CERTIFICATE OF CORRECTION

PATENT NO. : 6,291,678 B1
DATED : September 18, 2001
INVENTOR(S) : Berryman et al.

It is certified that error appears in the above-identified patent and that said Letters Patent is hereby corrected as shown below:

<u>Column 5,</u>
Line 40, "u is" should read -- u, p, and Z are --

<u>Column 6,</u>
Line 14, "u, R R$^{5a}$," should read -- u, R$^{5a}$, R$^5$ --

<u>Column 26,</u>
Line 43, "M+=1 608" should read -- M + 1 = 608 --

<u>Column 27,</u>
Line 33, "M+=1 507" should read -- M + 1 = 507 --

<u>Column 31,</u>
Line 32, "M+=1 424" should read -- M + 1 = 424 --

<u>Column 35,</u>
Line 54, "M+=1 126" should read -- M + 1 = 126 --

<u>Column 36,</u>
Line 42, "M+=1 648" should read -- M + 1 = 648 --

<u>Column 56,</u>
Line 33, after "X is O, or" insert -- S --.

<u>Column 61,</u>
Lines 20-30, "wherein X is O, or

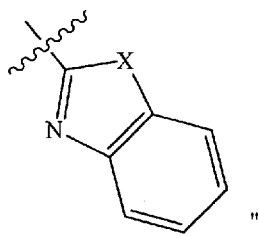

"

should read -- wherein X is O or S, --

UNITED STATES PATENT AND TRADEMARK OFFICE
CERTIFICATE OF CORRECTION

PATENT NO. : 6,291,678 B1
DATED : September 18, 2001
INVENTOR(S) : Berryman et al.

It is certified that error appears in the above-identified patent and that said Letters Patent is hereby corrected as shown below:

Column 62,
Lines 41-49, "wherein Z is as defined above,

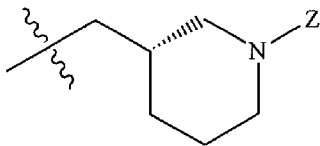

and $R^3$ is $CO_2$t-Bu." should read

-- 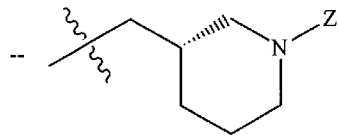

wherein Z is as defined above,
and $R^3$ is $CO_2$t-Bu. --

Signed and Sealed this

Twenty-sixth Day of November, 2002

Attest:

JAMES E. ROGAN
Attesting Officer *Director of the United States Patent and Trademark Office*

UNITED STATES PATENT AND TRADEMARK OFFICE
CERTIFICATE OF CORRECTION

PATENT NO.    : 6,291,678 B1                                       Page 1 of 1
DATED         : September 18, 2001
INVENTOR(S)   : Berryman et al.

It is certified that error appears in the above-identified patent and that said Letters Patent is hereby corrected as shown below:

Column 58,
Line 24, "wherein u, p, and z are as defined above," should read -- wherein u, p, and Z are as defined above, --
Line 34, "wherein u, p, and z are as defined above," should read -- wherein u, p, and Z are as defined above, --

Signed and Sealed this

Eighth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,291,678 B1 Page 1 of 1
DATED : September 18, 2001
INVENTOR(S) : Berryman et al.

It is certified that error appears in the above-identified patent and that said Letters Patent is hereby corrected as shown below:

Column 56,
Line 33, "X is O, or" should read -- X is O or --
Line 48, "$R^5$ is as defined above," should read -- $R^5$ is H, alkyl, alkenyl, alkynyl, cycloalkyl, cycloalkylalkyl, aryl, or arylalkyl, --

Column 57,
Line 11, "$R^5$, $R^{5a}$," should read -- $R^5$ and $R^{5a}$ are the same or different and are as defined above for $R^5$, --
Line 34, "y" should read -- Y --

Signed and Sealed this

Sixteenth Day of March, 2004

JON W. DUDAS
*Acting Director of the United States Patent and Trademark Office*